US00RE45870E

(19) United States
(12) Reissued Patent
Wang et al.

(10) Patent Number: US RE45,870 E
(45) Date of Reissued Patent: Jan. 26, 2016

(54) APPARATUS AND METHOD FOR PATIENT ROUNDING WITH A REMOTE CONTROLLED ROBOT

(75) Inventors: Yulun Wang, Goleta, CA (US); Louis Kavoussi, Lutherville, MD (US)

(73) Assignee: InTouch Technologies, Inc., Santa Barbara, CA (US)

(21) Appl. No.: 13/543,225

(22) Filed: Jul. 6, 2012

Related U.S. Patent Documents

Reissue of:
(64) Patent No.: 7,289,883
Issued: Oct. 30, 2007
Appl. No.: 11/650,149
Filed: Jan. 5, 2007

U.S. Applications:
(63) Continuation of application No. 10/751,032, filed on Jan. 2, 2004, now Pat. No. 7,164,969, which is a continuation-in-part of application No. 10/206,457, filed on Jul. 25, 2002, now Pat. No. 6,925,357.

(51) Int. Cl.
*B25J 5/00* (2006.01)
*B25J 9/18* (2006.01)
(Continued)

(52) U.S. Cl.
CPC ..... *G06F 19/3418* (2013.01); *B25J 5/007* (2013.01); *B25J 9/0003* (2013.01); *B25J 9/162* (2013.01);
(Continued)

(58) Field of Classification Search
CPC ..... G06F 19/3418; B25J 5/007; B25J 9/1689; H04N 7/185
USPC ..... 700/245, 246, 250, 254, 260, 261, 262; 318/568.12; 901/1, 2; 702/188
See application file for complete search history.

(56) References Cited

U.S. PATENT DOCUMENTS 3,821,995 A 7/1974 Aghnides
4,413,693 A 11/1983 Derby
(Continued)

FOREIGN PATENT DOCUMENTS

CA 2289697 A1 1/1998
CA 2289697 11/1998
(Continued)

OTHER PUBLICATIONS

Nakajima et al., "A Multimedia Teleteaching System Using an Electronic Whiteboard forTwo-Way Communication of Motion Videos and Chalkboards", 1993, IEEE, p. 436-441.*
(Continued)

*Primary Examiner* — James Trammell
*Assistant Examiner* — David Testardi
(74) *Attorney, Agent, or Firm* — Knobbe Martens Olson & Bear LLP

(57) ABSTRACT

A method for remotely monitoring a patient. The method includes generating and transmitting input commands to the robot from a remote station. The remote station may include a personal computer that is operated by a doctor. The input commands can move the robot so that a video image and sounds of the patient can be captured by a robot camera and microphone, respectively, and transmitted back to the remote station. The robot may also have a monitor and a speaker to allow for two-way videoconferencing between the patient and a doctor at the remote station. The robot can move from room to room so that a doctor can make "patient rounds" within a medical facility. The system thus allows a doctor visit patients from a remote location, thereby improving the frequency of visits and the quality of medical care.

REEXAMINATION RESULTS

The questions raised in reexamination proceeding No. 90/012,069, filed Dec. 22, 2011, have been considered, and the results thereof are reflected in this reissue patent which constitutes the reexamination certificate required by 35 U.S.C. 307 as provided in 37 CFR 1.570(e) for *ex parte* reexaminations, or the reexamination certificate required by 35 U.S.C. 316 as provided in 37 CFR 1.997(e) for *inter partes* reexaminations.

53 Claims, 10 Drawing Sheets

(51) Int. Cl.

| | |
|---|---|
| ***G06F 19/00*** | (2011.01) |
| ***B25J 9/16*** | (2006.01) |
| ***G05D 1/00*** | (2006.01) |
| ***B25J 19/02*** | (2006.01) |
| ***B25J 9/00*** | (2006.01) |
| ***B25J 11/00*** | (2006.01) |
| ***G05D 1/02*** | (2006.01) |
| *H04N 7/18* | (2006.01) |

(52) U.S. Cl.

CPC ..... *B25J 9/1689* (2013.01); *B25J 11/0005* (2013.01); *B25J 19/023* (2013.01); *G05D 1/0038* (2013.01); *G05D 1/0225* (2013.01); *B25J 9/1602* (2013.01); *B25J 9/163* (2013.01); *B25J 9/1633* (2013.01); *B25J 9/1692* (2013.01); *G05D 2201/0206* (2013.01); *G05D 2201/0211* (2013.01); *H04N 7/185* (2013.01)

(56) References Cited

U.S. PATENT DOCUMENTS 4,471,354 A 9/1984 Smith
4,519,466 A 5/1985 Shiraishi
4,572,594 A 2/1986 Schwartz
4,625,274 A 11/1986 Schroeder
4,638,445 A 1/1987 Mattaboni
4,652,204 A 3/1987 Arnett
4,669,168 A 6/1987 Tamura et al.
4,679,152 A * 7/1987 Perdue ..... 701/23
4,697,472 A 10/1987 Hiyane
4,709,265 A 11/1987 Silverman et al.
4,733,737 A 3/1988 Falamak
4,751,658 A 6/1988 Kadonoff et al.
4,766,581 A 8/1988 Korn et al.
4,777,416 A 10/1988 George et al.
4,797,557 A 1/1989 Ohman
4,803,625 A 2/1989 Fu et al.
4,847,764 A 7/1989 Halvorson
4,875,172 A 10/1989 Kanayama
4,942,512 A 7/1990 Kohno
4,942,538 A 7/1990 Yuan et al.
4,953,159 A 8/1990 Hayden et al.
4,974,607 A 12/1990 Miwa
4,977,971 A 12/1990 Crane, III et al.
5,006,988 A 4/1991 Borenstein et al.
5,040,116 A 8/1991 Evans, Jr. et al.
5,051,906 A 9/1991 Evans et al.
5,073,749 A 12/1991 Kanayama
5,084,828 A 1/1992 Kaufman et al.
5,130,794 A 7/1992 Ritchey
5,148,591 A 9/1992 Pryor
5,153,833 A 10/1992 Gordon et al.
5,155,684 A 10/1992 Burke et al.
5,157,491 A 10/1992 Kassatly
5,182,641 A 1/1993 Diner et al.
5,186,270 A 2/1993 West
5,193,143 A 3/1993 Kaemmerer et al.
5,217,453 A 6/1993 Wilk
5,220,263 A * 6/1993 Onishi et al. ..... 318/587
5,224,157 A 6/1993 Yamada et al.
5,231,693 A 7/1993 Backes et al.
5,236,432 A 8/1993 Matsen, III et al.
5,305,427 A 4/1994 Nagata
5,315,287 A 5/1994 Sol
5,319,611 A 6/1994 Korba
5,341,242 A 8/1994 Gilboa et al.
5,341,457 A 8/1994 Hall, II et al.
5,341,459 A 8/1994 Backes
5,341,854 A 8/1994 Zezulka et al.
5,347,457 A 9/1994 Tanaka et al.
5,350,033 A 9/1994 Kraft
5,366,896 A 11/1994 Margrey
5,374,879 A 12/1994 Pin et al.
5,400,068 A * 3/1995 Ishida et al. ..... 348/14.04
5,417,210 A 5/1995 Funda et al.
5,419,008 A 5/1995 West
5,436,542 A 7/1995 Petelin et al.
5,153,833 B1 8/1995 Gordon et al.
5,441,042 A 8/1995 Putman
5,441,047 A 8/1995 David et al.
5,442,728 A 8/1995 Kaufman
5,462,051 A 10/1995 Oka et al.
5,486,853 A 1/1996 Baxter et al.
5,510,832 A 4/1996 Garcia
5,528,289 A 6/1996 Cortjens et al.
5,539,741 A 7/1996 Barraclough et al.
5,544,649 A 8/1996 David et al. ..... 600/301
5,550,577 A 8/1996 Verbiest et al.
5,553,609 A 9/1996 Chen et al.
5,572,229 A 11/1996 Fisher
5,572,999 A 11/1996 Funda et al.
5,594,859 A 1/1997 Palmer et al.
5,600,573 A 2/1997 Hendricks et al.
5,619,341 A * 4/1997 Auyeung et al. ..... 358/404
5,630,566 A 5/1997 Case
5,636,218 A 6/1997 Ishikawa et al.
5,652,849 A 7/1997 Conway et al.
5,657,246 A 8/1997 Hogan et al.
5,659,779 A 8/1997 Laird et al.
5,673,082 A 9/1997 Wells et al.
5,682,199 A 10/1997 Lankford
5,684,695 A 11/1997 Bauer
5,701,904 A 12/1997 Simmons et al.
5,739,657 A 4/1998 Takayama et al.
5,749,058 A 5/1998 Hashimoto
5,749,362 A 5/1998 Funda et al.
5,762,458 A 6/1998 Wang et al.
5,764,731 A 6/1998 Yablon
5,767,897 A 6/1998 Howell
5,786,846 A 7/1998 Hiroaki
5,801,755 A * 9/1998 Echerer ..... 348/14.01
5,802,494 A 9/1998 Kuno
5,836,872 A 11/1998 Kenet et al.
5,838,575 A 11/1998 Lion
5,844,599 A * 12/1998 Hildin ..... 348/14.1
5,857,534 A 1/1999 DeVault et al.
5,867,653 A 2/1999 Aras et al.
5,871,451 A 2/1999 Unger et al.
5,872,451 A 2/1999 Guzik
5,872,922 A * 2/1999 Hogan et al. ..... 709/204
5,876,325 A 3/1999 Mizuno et al.
5,911,036 A 6/1999 Wright et al.
5,917,958 A 6/1999 Nunally et al.
5,927,423 A 7/1999 Wada et al.
5,949,758 A 9/1999 Kober et al.
5,954,692 A 9/1999 Smith et al.
5,959,423 A 9/1999 Nakanishi et al.
5,961,446 A * 10/1999 Beller et al. ..... 600/300
5,966,130 A 10/1999 Benman, Jr.
5,973,724 A 10/1999 Riddle
5,974,446 A 10/1999 Sonnenreich et al.
5,983,263 A 11/1999 Rothrock et al.
5,995,884 A 11/1999 Allen et al.
5,999,977 A 12/1999 Riddle
6,006,946 A 12/1999 Williams et al.
6,036,812 A 3/2000 Williams et al.
6,047,259 A 4/2000 Campbell et al.
6,133,944 A 10/2000 Braun et al.
6,135,228 A 10/2000 Asada et al.
6,148,100 A 11/2000 Anderson et al.
6,170,929 B1 1/2001 Wilson et al.
6,175,779 B1 1/2001 Barrett
6,189,034 B1 * 2/2001 Riddle ..... 709/227
6,201,984 B1 3/2001 Funda et al.
6,211,903 B1 4/2001 Bullister
6,219,587 B1 4/2001 Ahlin et al.
6,232,735 B1 5/2001 Baba et al.
6,233,504 B1 5/2001 Das et al.
6,233,735 B1 5/2001 Ebihara
6,256,556 B1 7/2001 Zenke
6,259,806 B1 7/2001 Green
6,259,956 B1 7/2001 Myers et al.
6,266,162 B1 7/2001 Okamura et al.

(56) References Cited

U.S. PATENT DOCUMENTS 6,266,577 B1 7/2001 Popp et al.
6,289,263 B1 9/2001 Mukherjee
6,292,713 B1 9/2001 Jouppi et al.
6,304,050 B1 10/2001 Skaar et al.
6,317,652 B1 * 11/2001 Osada ..... 700/245
6,321,137 B1 11/2001 De Smet
6,325,756 B1 12/2001 Webb et al.
6,327,516 B1 12/2001 Zenke
6,330,486 B1 12/2001 Padula
6,330,493 B1 12/2001 Takahashi et al.
6,346,950 B1 2/2002 Jouppi
6,346,962 B1 2/2002 Goodridge
6,369,847 B1 4/2002 James et al.
6,381,515 B1 4/2002 Inoue et al.
6,389,329 B1 * 5/2002 Colens ..... 700/262
6,400,378 B1 6/2002 Snook
6,408,230 B2 6/2002 Wada
6,430,471 B1 8/2002 Kintou et al.
6,430,475 B2 8/2002 Okamoto et al.
6,438,457 B1 8/2002 Yokoo et al.
6,452,915 B1 9/2002 Jorgensen
6,457,043 B1 9/2002 Kwak et al.
6,459,955 B1 10/2002 Bartsch et al.
6,463,352 B1 10/2002 Tadokoro et al.
6,463,361 B1 10/2002 Wang et al.
6,466,844 B1 10/2002 Ikeda et al.
6,468,265 B1 10/2002 Evans et al.
6,474,434 B1 11/2002 Bech
6,480,762 B1 11/2002 Uchikubo et al.
6,491,701 B2 12/2002 Tierney et al.
6,496,099 B2 12/2002 Wang et al.
6,496,755 B2 12/2002 Wallach et al.
6,501,740 B1 12/2002 Sun et al.
6,507,773 B2 1/2003 Parker et al.
6,522,906 B1 2/2003 Salisbury et al.
6,523,629 B1 2/2003 Buttz et al.
6,526,332 B2 2/2003 Sakamoto et al.
6,529,765 B1 3/2003 Franck
6,529,802 B1 3/2003 Kawakita et al.
6,532,404 B2 3/2003 Colens
6,535,182 B2 3/2003 Stanton
6,535,793 B2 3/2003 Allard
6,540,039 B1 4/2003 Yu
6,543,899 B2 4/2003 Covannon et al.
6,549,215 B2 4/2003 Jouppi
6,563,533 B1 5/2003 Colby
6,580,246 B2 6/2003 Jacobs
6,581,798 B2 6/2003 Liff et al.
6,584,376 B1 6/2003 Van Kommer
6,587,750 B2 7/2003 Gerbi et al.
6,590,604 B1 * 7/2003 Tucker et al. ..... 348/14.13
6,594,269 B1 7/2003 Polcyn
6,594,552 B1 7/2003 Nowlin et al.
6,602,469 B1 8/2003 Maus et al.
6,604,019 B2 8/2003 Ahlin et al.
6,604,021 B2 8/2003 Imai et al.
6,611,120 B2 8/2003 Song et al.
6,646,677 B2 11/2003 Noro et al.
6,650,748 B1 11/2003 Edwards et al.
6,666,374 B1 12/2003 Green et al.
6,684,129 B2 1/2004 Salisbury et al.
6,691,000 B2 2/2004 Nagai et al.
6,710,797 B1 3/2004 McNelley et al.
6,724,823 B2 * 4/2004 Rovati et al. ..... 375/240.17
6,728,599 B2 4/2004 Wang et al.
6,763,282 B2 7/2004 Glenn et al.
6,764,373 B1 7/2004 Osawa et al.
6,769,771 B2 8/2004 Trumbull
6,781,606 B2 8/2004 Jouppi
6,784,916 B2 8/2004 Smith
6,785,589 B2 8/2004 Eggenberger et al.
6,791,550 B2 9/2004 Goldhor et al.
6,798,753 B1 9/2004 Doganata et al.
6,799,065 B1 9/2004 Niemeyer
6,799,088 B2 9/2004 Wang et al.
6,804,580 B1 10/2004 Stoddard et al.
6,804,656 B1 10/2004 Rosenfeld et al.
6,810,411 B1 10/2004 Coughlin et al.
6,816,192 B1 * 11/2004 Nishikawa ..... 348/231.99
6,836,703 B2 12/2004 Wang et al.
6,839,612 B2 1/2005 Sanchez et al.
6,840,904 B2 1/2005 Goldberg
6,845,297 B2 1/2005 Allard
6,852,107 B2 2/2005 Wang et al.
6,853,878 B2 2/2005 Hirayama et al.
6,853,880 B2 2/2005 Sakagami et al.
6,871,117 B2 3/2005 Wang et al.
6,879,879 B2 4/2005 Jouppi et al.
6,888,333 B2 5/2005 Laby
6,892,112 B2 5/2005 Wang et al.
6,895,305 B2 5/2005 Lathan et al.
6,898,484 B2 5/2005 Lemelson et al.
6,914,622 B1 7/2005 Smith et al.
6,925,357 B2 8/2005 Wang et al.
6,951,535 B2 10/2005 Ghodoussi et al.
6,952,470 B1 10/2005 Tioe
6,957,712 B2 * 10/2005 Song et al. ..... 180/167
6,958,706 B2 10/2005 Chaco et al.
6,965,394 B2 11/2005 Gutta et al.
6,995,664 B1 2/2006 Darling
7,030,757 B2 4/2006 Matsuhira et al.
7,058,689 B2 6/2006 Parker et al.
7,092,001 B2 8/2006 Schulz
7,096,090 B1 8/2006 Zweig
7,115,102 B2 10/2006 Abbruscato
7,117,067 B2 10/2006 McLurkin et al.
7,123,285 B2 10/2006 Smith et al.
7,123,974 B1 10/2006 Hamilton
7,123,991 B2 10/2006 Graf et al.
7,127,325 B2 10/2006 Nagata et al.
7,129,970 B2 10/2006 James et al.
7,133,062 B2 11/2006 Castles et al.
7,142,945 B2 11/2006 Wang et al.
7,142,947 B2 11/2006 Wang et al.
7,151,982 B2 12/2006 Liff
7,154,526 B2 12/2006 Foote et al.
7,155,306 B2 12/2006 Haitin et al.
7,156,809 B2 1/2007 Quy
7,158,859 B2 1/2007 Wang et al.
7,158,860 B2 1/2007 Wang et al.
7,161,322 B2 1/2007 Wang et al.
7,162,338 B2 1/2007 Goncalves et al.
7,164,969 B2 1/2007 Wang et al.
7,171,286 B2 1/2007 Wang et al.
7,174,238 B1 2/2007 Zweig
7,184,559 B2 2/2007 Jouppi
7,188,000 B2 3/2007 Chiappetta et al.
7,199,790 B2 4/2007 Rosenberg et al.
7,202,851 B2 4/2007 Cunningham et al.
7,206,627 B2 4/2007 Abovitz et al.
7,215,786 B2 5/2007 Nakadai et al.
7,219,364 B2 * 5/2007 Bolle et al. ..... 725/105
7,227,334 B2 6/2007 Yang et al.
7,256,708 B2 8/2007 Rosenfeld et al.
7,262,573 B2 8/2007 Wang et al.
7,283,153 B2 * 10/2007 Provost et al. ..... 348/14.01
7,289,883 B2 10/2007 Wang et al.
7,292,912 B2 11/2007 Wang et al.
7,321,807 B2 1/2008 Laski
7,346,429 B2 3/2008 Goldenberg et al.
7,382,399 B1 6/2008 McCall
7,386,730 B2 6/2008 Uchikubo
7,391,432 B2 6/2008 Terado
7,404,140 B2 7/2008 O'Rourke
7,432,949 B2 10/2008 Remy et al.
7,441,953 B2 10/2008 Banks
7,525,281 B2 4/2009 Koyanagi et al.
7,535,486 B2 5/2009 Motomura et al.
7,593,030 B2 9/2009 Wang et al.
7,624,166 B2 11/2009 Foote et al.
7,647,320 B2 1/2010 Mok et al.
7,719,229 B2 5/2010 Kaneko et al.
7,761,185 B2 7/2010 Wang et al.
7,769,492 B2 8/2010 Wang et al.

(56) References Cited

U.S. PATENT DOCUMENTS 7,813,836 B2 10/2010 Wang et al.
7,831,575 B2 11/2010 Trossell et al.
7,835,775 B2 11/2010 Sawayama et al.
7,860,680 B2 12/2010 Arms et al.
RE42,288 E 4/2011 Degioanni
7,924,323 B2 4/2011 Walker et al.
7,982,763 B2 7/2011 King
8,077,963 B2 12/2011 Wang et al.
8,116,910 B2 2/2012 Walters et al.
8,170,241 B2 5/2012 Roe et al.
8,179,418 B2 5/2012 Wright et al.
8,180,486 B2 5/2012 Saito et al.
8,209,051 B2 6/2012 Wang et al.
8,265,793 B2 * 9/2012 Cross et al. ..... 700/259
8,348,675 B2 * 1/2013 Dohrmann ..... 434/326
2001/0002448 A1 5/2001 Wilson et al.
2001/0010053 A1 7/2001 Ben-Shachar et al.
2001/0034475 A1 10/2001 Flach et al.
2001/0034544 A1 10/2001 Mo
2001/0037163 A1 11/2001 Allard
2001/0051881 A1 12/2001 Filler
2001/0054071 A1 12/2001 Loeb ..... 709/205
2001/0055373 A1 12/2001 Yamashita
2002/0010596 A1 * 1/2002 Matory ..... 705/2
2002/0015296 A1 2/2002 Howell et al.
2002/0027597 A1 3/2002 Sachau
2002/0049517 A1 4/2002 Ruffner
2002/0055917 A1 5/2002 Muraca
2002/0057279 A1 5/2002 Jouppi
2002/0058929 A1 5/2002 Green
2002/0059587 A1 5/2002 Cofano et al.
2002/0063726 A1 5/2002 Jouppi
2002/0073429 A1 6/2002 Beane et al.
2002/0082498 A1 6/2002 Wendt et al.
2002/0095238 A1 7/2002 Ahlin et al.
2002/0098879 A1 7/2002 Rheey
2002/0104094 A1 8/2002 Alexander et al.
2002/0106998 A1 * 8/2002 Presley et al. ..... 455/403
2002/0109770 A1 8/2002 Terada
2002/0111988 A1 8/2002 Sato
2002/0120362 A1 8/2002 Lathan et al.
2002/0130950 A1 9/2002 James et al.
2002/0141595 A1 10/2002 Jouppi
2002/0143923 A1 10/2002 Alexander
2002/0177925 A1 11/2002 Onishi et al.
2002/0183894 A1 12/2002 Wang et al.
2002/0184674 A1 12/2002 Xi et al.
2002/0186243 A1 12/2002 Ellis et al.
2003/0030397 A1 2/2003 Simmons
2003/0048481 A1 3/2003 Kobayashi et al.
2003/0050733 A1 3/2003 Wang et al.
2003/0060808 A1 3/2003 Wilk
2003/0063600 A1 4/2003 Noma et al.
2003/0069752 A1 4/2003 Ledain et al.
2003/0100892 A1 5/2003 Morley et al.
2003/0104806 A1 6/2003 Ruef et al.
2003/0114962 A1 6/2003 Niemeyer
2003/0126361 A1 7/2003 Slater et al.
2003/0135203 A1 7/2003 Wang et al.
2003/0144579 A1 7/2003 Buss
2003/0144649 A1 7/2003 Ghodoussi et al.
2003/0151658 A1 8/2003 Smith
2003/0171710 A1 9/2003 Bassuk et al.
2003/0174285 A1 9/2003 Trumbull
2003/0180697 A1 9/2003 Kim et al.
2003/0199000 A1 10/2003 Valkirs et al.
2003/0206242 A1 11/2003 Choi et al.
2003/0216834 A1 11/2003 Allard
2003/0220541 A1 11/2003 Salisbury et al.
2003/0220715 A1 11/2003 William et al.
2003/0231244 A1 12/2003 Bonilla et al.
2003/0232649 A1 12/2003 Gizis
2004/0010344 A1 1/2004 Hiratsuka
2004/0012362 A1 1/2004 Tsurumi
2004/0013295 A1 1/2004 Sabe et al.
2004/0019406 A1 1/2004 Wang et al.
2004/0024490 A1 2/2004 McLurkin et al.
2004/0041904 A1 3/2004 Lapalme et al.
2004/0065073 A1 4/2004 Nash
2004/0068657 A1 4/2004 Alexander et al.
2004/0078219 A1 4/2004 Kaylor et al.
2004/0080610 A1 4/2004 James et al.
2004/0088077 A1 5/2004 Jouppi et al.
2004/0093409 A1 5/2004 Thompson et al.
2004/0098167 A1 5/2004 Yi et al.
2004/0102167 A1 5/2004 Shim et al.
2004/0117065 A1 6/2004 Wang et al.
2004/0135879 A1 7/2004 Stacy et al.
2004/0138547 A1 7/2004 Wang et al.
2004/0143421 A1 * 7/2004 Wang et al. ..... 702/188
2004/0148638 A1 7/2004 Weisman et al.
2004/0153211 A1 8/2004 Kamoto et al.
2004/0157612 A1 8/2004 Kim
2004/0162637 A1 * 8/2004 Wang et al. ..... 700/245
2004/0167666 A1 8/2004 Wang et al.
2004/0167668 A1 8/2004 Wang et al.
2004/0170300 A1 9/2004 Jouppi
2004/0172301 A1 9/2004 Mihai et al.
2004/0174129 A1 9/2004 Wang et al.
2004/0175684 A1 9/2004 Kaasa et al.
2004/0179714 A1 9/2004 Jouppi
2004/0189700 A1 9/2004 Mandavilli et al.
2004/0201602 A1 10/2004 Mody et al.
2004/0205664 A1 10/2004 Prendergast
2004/0215490 A1 10/2004 Duchon et al.
2004/0222638 A1 11/2004 Bednyak
2004/0224676 A1 11/2004 Iseki
2004/0230340 A1 11/2004 Fukuchi et al.
2004/0240981 A1 12/2004 Dothan et al.
2004/0241981 A1 12/2004 Doris et al.
2005/0003330 A1 1/2005 Asgarinejad et al.
2005/0007445 A1 1/2005 Foote et al.
2005/0013149 A1 1/2005 Trossell
2005/0021182 A1 1/2005 Wang
2005/0021183 A1 1/2005 Wang et al.
2005/0021187 A1 1/2005 Wang et al.
2005/0021309 A1 1/2005 Alexander et al.
2005/0024485 A1 2/2005 Castles et al.
2005/0027567 A1 2/2005 Taha
2005/0027794 A1 2/2005 Decker
2005/0028221 A1 2/2005 Liu et al.
2005/0035862 A1 2/2005 Wildman et al.
2005/0038416 A1 2/2005 Wang et al.
2005/0038564 A1 2/2005 Burick et al.
2005/0049898 A1 3/2005 Hirakawa
2005/0052527 A1 3/2005 Remy et al.
2005/0065435 A1 3/2005 Rauch et al.
2005/0065438 A1 3/2005 Miller
2005/0065659 A1 3/2005 Tanaka
2005/0065813 A1 3/2005 Mishelevich et al.
2005/0071046 A1 3/2005 Miyazaki et al.
2005/0078816 A1 4/2005 Sekiguchi et al.
2005/0083011 A1 4/2005 Yang et al.
2005/0099493 A1 5/2005 Chew
2005/0104964 A1 5/2005 Bovyrin et al.
2005/0110867 A1 5/2005 Schulz
2005/0122390 A1 6/2005 Wang et al.
2005/0154265 A1 7/2005 Miro et al.
2005/0182322 A1 8/2005 Grispo
2005/0192721 A1 9/2005 Jouppi
2005/0204438 A1 9/2005 Wang et al.
2005/0212478 A1 9/2005 Takenaka
2005/0219356 A1 10/2005 Smith et al.
2005/0225634 A1 10/2005 Brunetti et al.
2005/0231156 A1 10/2005 Yan
2005/0232647 A1 10/2005 Takenaka
2005/0267826 A1 12/2005 Levy et al.
2005/0283414 A1 12/2005 Fernandes et al.
2006/0007943 A1 1/2006 Fellman
2006/0013263 A1 1/2006 Fellman
2006/0013469 A1 1/2006 Wang et al.
2006/0013488 A1 1/2006 Inoue
2006/0029065 A1 2/2006 Fellman
2006/0047365 A1 * 3/2006 Ghodoussi et al. ..... 700/251

(56) References Cited

U.S. PATENT DOCUMENTS

| | | | |
|---|---|---|---|
| 2006/0048286 | A1 | 3/2006 | Donato |
| 2006/0052676 | A1 | 3/2006 | Wang et al. |
| 2006/0052684 | A1 | 3/2006 | Takahashi et al. |
| 2006/0064212 | A1 | 3/2006 | Thorne |
| 2006/0074525 | A1 | 4/2006 | Close et al. |
| 2006/0074719 | A1 | 4/2006 | Horner |
| 2006/0082642 | A1 | 4/2006 | Wang et al. |
| 2006/0087746 | A1 | 4/2006 | Lipow |
| 2006/0095158 | A1 | 5/2006 | Lee et al. |
| 2006/0095170 | A1 | 5/2006 | Yang et al. |
| 2006/0098573 | A1 | 5/2006 | Beer et al. |
| 2006/0103659 | A1 | 5/2006 | Karandikar et al. |
| 2006/0104279 | A1 | 5/2006 | Fellman et al. |
| 2006/0106493 | A1 | 5/2006 | Niemeyer et al. |
| 2006/0122482 | A1 | 6/2006 | Mariotti et al. |
| 2006/0142983 | A1 | 6/2006 | Sorensen et al. |
| 2006/0161303 | A1 | 7/2006 | Wang et al. |
| 2006/0164546 | A1 | 7/2006 | Adachi et al. |
| 2006/0173712 | A1 | 8/2006 | Joubert |
| 2006/0178776 | A1 | 8/2006 | Feingold et al. |
| 2006/0189393 | A1 | 8/2006 | Edery |
| 2006/0195569 | A1 | 8/2006 | Barker |
| 2006/0259193 | A1 | 11/2006 | Wang et al. |
| 2006/0293788 | A1 | 12/2006 | Pogodin |
| 2007/0021871 | A1 | 1/2007 | Wang et al. |
| 2007/0046237 | A1 | 3/2007 | Lakshmanan et al. |
| 2007/0050937 | A1 | 3/2007 | Song et al. |
| 2007/0064092 | A1 | 3/2007 | Sandberg et al. |
| 2007/0078566 | A1 | 4/2007 | Wang et al. |
| 2007/0112700 | A1 | 5/2007 | Den et al. |
| 2007/0117516 | A1 | 5/2007 | Saidi et al. |
| 2007/0120965 | A1 | 5/2007 | Sandberg et al. |
| 2007/0122783 | A1 | 5/2007 | Habashi |
| 2007/0135967 | A1 | 6/2007 | Jung et al. |
| 2007/0142964 | A1 | 6/2007 | Abramson |
| 2007/0176060 | A1 | 8/2007 | White et al. |
| 2007/0192910 | A1 | 8/2007 | Vu et al. |
| 2007/0197896 | A1 | 8/2007 | Moll et al. |
| 2007/0198128 | A1 | 8/2007 | Ziegler et al. |
| 2007/0199108 | A1 | 8/2007 | Angle et al. |
| 2007/0216347 | A1 | 9/2007 | Kaneko et al. |
| 2007/0250212 | A1 | 10/2007 | Halloran et al. |
| 2007/0262884 | A1 | 11/2007 | Goncalves et al. |
| 2007/0273751 | A1 | 11/2007 | Sachau |
| 2007/0291109 | A1 | 12/2007 | Wang et al. |
| 2007/0291128 | A1 | 12/2007 | Wang et al. |
| 2008/0011904 | A1 | 1/2008 | Cepollina et al. |
| 2008/0065268 | A1 | 3/2008 | Wang et al. |
| 2008/0082211 | A1 | 4/2008 | Wang et al. |
| 2008/0126132 | A1 | 5/2008 | Warner et al. |
| 2008/0133052 | A1 | 6/2008 | Jones et al. |
| 2008/0201017 | A1 | 8/2008 | Wang et al. |
| 2008/0215987 | A1 | 9/2008 | Alexander et al. |
| 2008/0229531 | A1 | 9/2008 | Takida |
| 2008/0255703 | A1 | 10/2008 | Wang et al. |
| 2008/0263451 | A1 | 10/2008 | Portele et al. |
| 2008/0269949 | A1 | 10/2008 | Norman et al. |
| 2008/0281467 | A1 | 11/2008 | Pinter |
| 2009/0030552 | A1 | 1/2009 | Nakadai et al. |
| 2009/0055023 | A1 | 2/2009 | Walters et al. |
| 2009/0070135 | A1 | 3/2009 | Parida et al. |
| 2009/0105882 | A1 | 4/2009 | Wang et al. |
| 2009/0125147 | A1 | 5/2009 | Wang et al. |
| 2009/0164255 | A1 | 6/2009 | Menschik et al. |
| 2009/0237317 | A1 | 9/2009 | Rofougaran |
| 2009/0240371 | A1 | 9/2009 | Wang et al. |
| 2009/0259339 | A1 | 10/2009 | Wright et al. |
| 2010/0010672 | A1 | 1/2010 | Wang et al. |
| 2010/0010673 | A1 | 1/2010 | Wang et al. |
| 2010/0019715 | A1 | 1/2010 | Roe et al. |
| 2010/0063848 | A1 | 3/2010 | Kremer et al. |
| 2010/0070079 | A1 | 3/2010 | Mangaser et al. |
| 2010/0073490 | A1 | 3/2010 | Wang et al. |
| 2010/0076600 | A1 | 3/2010 | Cross et al. |
| 2010/0088232 | A1 | 4/2010 | Gale |
| 2010/0115418 | A1 | 5/2010 | Wang et al. |
| 2010/0116566 | A1 | 5/2010 | Ohm et al. |
| 2010/0131103 | A1 | 5/2010 | Herzog et al. |
| 2010/0191375 | A1 | 7/2010 | Wright et al. |
| 2010/0268383 | A1 | 10/2010 | Wang et al. |
| 2010/0323783 | A1 | 12/2010 | Nonaka et al. |
| 2011/0050841 | A1 | 3/2011 | Wang et al. |
| 2011/0071702 | A1 | 3/2011 | Wang et al. |
| 2011/0172822 | A1 | 7/2011 | Ziegler et al. |
| 2011/0187875 | A1 | 8/2011 | Sanchez et al. |
| 2011/0190930 | A1 | 8/2011 | Hanrahan et al. |
| 2011/0218674 | A1 | 9/2011 | Stuart et al. |
| 2011/0245973 | A1 | 10/2011 | Wang et al. |
| 2011/0292193 | A1 | 12/2011 | Wang et al. |
| 2011/0301759 | A1 | 12/2011 | Wang et al. |
| 2012/0023506 | A1 | 1/2012 | Maeckel et al. |
| 2012/0072023 | A1 | 3/2012 | Ota |
| 2012/0092157 | A1 | 4/2012 | Tran |

FOREIGN PATENT DOCUMENTS

| | | | | | |
|---|---|---|---|---|---|
| CA | 2289697 | A1 | | 11/1998 | |
| CN | 1554193 | A | | 12/2004 | |
| CN | 1554985 | A | | 12/2004 | |
| CN | 101106939 | A | | 1/2008 | |
| CN | 101390098 | A | | 3/2009 | |
| CN | 101507260 | A | | 8/2009 | |
| CN | 101730894 | A | | 6/2010 | |
| CN | 101866396 | A | | 10/2010 | |
| CN | 101978365 | A | | 2/2011 | |
| CN | 102203759 | A | | 9/2011 | |
| CN | 101106939 | B | | 11/2011 | |
| EP | 92/466492 | A2 | | 1/1992 | |
| EP | 92/488673 | A2 | | 6/1992 | |
| EP | 96/8084328 | A | | 3/1996 | |
| EP | 2002/0981905 | A2 | | 1/2002 | |
| EP | 0981905 | B1 | | 1/2002 | |
| EP | 2002/1262142 | A2 | | 12/2002 | |
| EP | 2004/1536660 | A3 | | 9/2004 | |
| EP | 2005/1536660 | A2 | | 6/2005 | |
| EP | 2005/1573406 | A2 | | 9/2005 | |
| EP | 2005/1594660 | A2 | | 11/2005 | |
| EP | 2007/1791464 | A2 | | 6/2007 | |
| EP | 2007/1800476 | A2 | | 6/2007 | |
| EP | 2007/1856644 | A2 | | 11/2007 | |
| EP | 2008/1928310 | A2 | | 6/2008 | |
| EP | 2009/2027716 | A2 | | 2/2009 | |
| EP | 2010/2145274 | A1 | | 1/2010 | |
| EP | 2010/2214111 | A2 | | 8/2010 | |
| EP | 2010/2263158 | A2 | | 12/2010 | |
| EP | 2011/2300930 | A2 | | 3/2011 | |
| EP | 2011/2342651 | A2 | | 7/2011 | |
| JP | 95/7213753 | A | | 8/1995 | |
| JP | 95/7248823 | A | | 9/1995 | |
| JP | 95/7257422 | A | | 9/1995 | |
| JP | 95/7257422 | A | | 10/1995 | |
| JP | 96/8084328 | A | | 3/1996 | |
| JP | 96/8320727 | A | | 12/1996 | |
| JP | 97/9267276 | A | | 9/1997 | |
| JP | 97/9267276 | A | | 10/1997 | |
| JP | 10079097 | A | | 3/1998 | |
| JP | 10288689 | A | | 10/1998 | |
| JP | 11220706 | A | * | 8/1999 | ..... H04N 7/14 |
| JP | 2000-032319 | A | | 1/2000 | |
| JP | 2000/049800 | A | | 2/2000 | |
| JP | 2000/079587 | A | | 3/2000 | |
| JP | 2000/196876 | A | | 7/2000 | |
| JP | 2001/188124 | A | | 4/2001 | |
| JP | 2001/125641 | A | | 5/2001 | |
| JP | 2001/147718 | A | | 5/2001 | |
| JP | 2001/179663 | A | | 7/2001 | |
| JP | 2001/198865 | A | | 7/2001 | |
| JP | 2001/198868 | A | | 7/2001 | |
| JP | 2001/199356 | A | | 7/2001 | |
| JP | 2002/000574 | A | | 1/2002 | |
| JP | 2002/046088 | | | 2/2002 | |
| JP | 2002/046088 | A | | 2/2002 | |
| JP | 2002/235423 | A | | 2/2002 | |
| JP | 2002/112970 | A | | 4/2002 | |

(56) References Cited

FOREIGN PATENT DOCUMENTS

| | | | | |
|---|---|---|---|---|
| JP | 2002/101333 | A | 5/2002 | |
| JP | 2002/305743 | A | 10/2002 | |
| JP | 2002-305743 | A | 10/2002 | |
| JP | 2002/355779 | A | 12/2002 | |
| JP | 2004/524824 | T | 8/2004 | |
| JP | 2004/261941 | A | 9/2004 | |
| JP | 2004/289379 | A | 10/2004 | |
| JP | 2005/028066 | A | 2/2005 | |
| JP | 2005/059170 | A | 3/2005 | |
| JP | 2006/508806 | A | 3/2006 | |
| JP | 2006/109094 | A | 4/2006 | |
| JP | 2006/224294 | A | 8/2006 | |
| JP | 2006/246438 | A | 9/2006 | |
| JP | 2007/081646 | A | 3/2007 | |
| JP | 2009/002542 | A | 2/2009 | |
| JP | 2010/064154 | A | 3/2010 | |
| JP | 2010/532109 | A | 9/2010 | |
| JP | 2010/246954 | A | 11/2010 | |
| KR | 2006/037979 | A | 3/2006 | |
| KR | 2006/0037979 | A | 5/2006 | |
| KR | 2009/0012542 | A | 2/2009 | |
| KR | 2010/009479 | A | 2/2010 | |
| KR | 2010/0019479 | A | 2/2010 | |
| KR | 2010/039037 | A | 12/2010 | |
| KR | 2010/0139037 | A | 12/2010 | |
| WO | 93/06690 | A1 | 1/1993 | |
| WO | 93/06690 | A1 | 4/1993 | |
| WO | WO 9742761 | A1 * | 11/1997 | ..... H04N 7/14 |
| WO | 98/51078 | A1 | 11/1998 | |
| WO | 99/67067 | A2 | 12/1999 | |
| WO | 00/33726 | A3 | 6/2000 | |
| WO | 03/077745 | A1 | 9/2003 | |
| WO | 2004/008738 | A1 | 1/2004 | |
| WO | 2004/012018 | A2 | 2/2004 | |
| WO | 2004/075456 | A2 | 9/2004 | |
| WO | 2006/012797 | A1 | 2/2006 | |
| WO | 2006/078611 | A1 | 4/2006 | |
| WO | 2006044847 | A2 | 4/2006 | |
| WO | 2007/041295 | A1 | 4/2007 | |
| WO | 2007/041295 | A2 | 4/2007 | |
| WO | 2007/041038 | A1 | 6/2007 | |
| WO | 2008/100272 | A2 | 8/2008 | |
| WO | 2008/100272 | A3 | 8/2008 | |
| WO | 2008/100272 | A3 | 10/2008 | |
| WO | 2009/117274 | A2 | 9/2009 | |
| WO | 2009/128997 | A1 | 10/2009 | |
| WO | 2009/145958 | A2 | 12/2009 | |
| WO | 2010/006205 | A1 | 1/2010 | |
| WO | 2010/006211 | A1 | 1/2010 | |
| WO | 2010/033666 | A1 | 3/2010 | |
| WO | 2010/047881 | A1 | 4/2010 | |
| WO | 2010/062798 | A1 | 6/2010 | |
| WO | 2010/065257 | A1 | 6/2010 | |
| WO | 2010/120407 | A1 | 10/2010 | |
| WO | 2011/028589 | A2 | 3/2011 | |
| WO | 2011/028589 | A3 | 4/2011 | |
| WO | 2011/097130 | A2 | 8/2011 | |
| WO | 2011/097132 | A2 | 8/2011 | |
| WO | 2011/109336 | A2 | 9/2011 | |
| WO | 2011/097132 | A3 | 12/2011 | |
| WO | 2011/149902 | A2 | 12/2011 | |
| WO | 2011/149902 | A3 | 12/2011 | |

OTHER PUBLICATIONS

Weiss et al., Pebbles: A Personal Technology for Meeting Educational, Social and Emotional Needs of Hospitalised Children. 2001, p. 157-168.*

Thrun et al. Probabilistic Algorithms and the Interactive Museum Tour-Guide Robot Minerva, 2000, Internet, p. 1-35.*

Roy, Nicholas, et al. "Towards personal service robots for the elderly." Workshop on Interactive Robots and Entertainment (Wire 2000), (vol. 25), Apr. 30-May 1, 2000, 7 pages, downloaded from http://www.ri.cmu.edu/pub_files/pub2/roy_nicholas_2000_1/roy_nicholas_2000_1.pdf.*

Schraft, R.D. et al., "Care-O-bot™: the concept of a system for assisting elderly or disabled persons in home environments", Fraunhofer IPA Paper ID: SS 004/5, Publication Date: Apr. 15, 1998, downloaded from: http://citeseerx.ist.psu.edu/viewdoc/summary?doi=10.1.1.28.3868.*

Hees, William, "Communications Design for a Remote Presence Robot", CSCI E-131b, Final Project, Jan. 14, 2002.*

CMU course 16x62, "Robot user's manual" (describing the Nomad Scout), Carnegie Mellon Uniersity, Google date: Feb. 1, 2001, downloaded from http://www.cs.cmu.edu/~illah/CLASSDOCS/roboman.pdf.*

Google translation of: Innovations Report, "From research project to television star: Care-O-bot in ZDF series", Sep. 28, 2001, on the Internet at: http://www.innovations-report.de/specials/printa.php?id=5157.*

Panusopone, Krit et al., "Performance comparison of MPEG-4 and H.263+ for streaming video applications", Circuits Systems Signal Processing, vol. 20 No. 3, 2001, pp. 293-309.*

"MPEG-4: a Powerful Standard for Use in Web and Television Environments", by Rob Koenen (KPN Research), Google Date: Jul. 1, 1998, 4 pages, downloaded from http://www.w3.org/Architecture/1998/06/Workshop/paper26/.*

"MPEG File Format Summary", Google Date: Feb. 1, 2001, 8 pages, downloaded from: http://www.fileformat.info/format/mpeg/egff.htm.*

ACM Digital Library Record, "Autonomous Robots vol. 11 Issue 1", Jul. 2001, downloaded from http://dl.acm.org/citation.cfm?id=591550&picked=prox&cfid=360891374&cftoken=35225929.*

Brenner, Pablo, "A technical tutorial on the IEEE 802.11 protocol", BreezeCOM Wireless Communications, copyright 1997, 24 pages.*

Library of Congress, MARC 21 Format for Classification Data, "008—Fixed-Length Data Elements (NR)", Jan. 2000, 14 pages, downloaded from http://www.loc.gov/marc/classification/cd008.html.*

Nomad Scout Users Manual, Nomadic Technologies, Software Version 2.7, Part No. DOC00004, Jul. 12, 1999, 59 pages.*

OskiCat Catalog Record, "Personal tele-embodiment / by Eric John Paulos", Results page and MARC Display, retrieved Jun. 17, 2014, UCB Library Catalog, 3 pages total.*

Paulos, Eric et al., "Personal Tele-Embodiment", published as Chapter 9 in Goldberg et al., ed., "Beyond webcams", MIT Press, Publication Date: Jan. 4, 2002, pp. 155-167.*

Paulos, Eric et al., "Social Tele-Embodiment: Understanding Presence", Autonomous Robots, vol. 11 Issue 1, Jul. 2001, Kluwer Academic Publishers, pp. 87-95.*

Paulos, Eric John, Introductory and cover pages from 2001 Dissertation ("Personal Tele-Embodiment") including Contents table, together with e-mails relating thereto from UC Berkeley Libraries, as shelved at UC Berkeley Engineering Library (Northern Regional library Facility); catalog date May 8, 2002; 25 pages total, including 4 pages of e-mails.*

Baltus, et al., *Towards Personal Service Robots for the Elderly,* Proceedings of the Workshop on Interactive Robotics and Entertainment, Pittsburgh, PA, 2000 http://www.cs.cmu.edu/~thrun/papers/thrun.nursebot-early.pdf.

Barrett, Video Conferencing Business Soars as Companies Cut Travel; Some Travel Cuts Are Permanent, http://www.ivci.com/international_videoconferencing_news_videoconferencing_news_19.html, May 13, 2002.

Chen, et al., *Collaborative Teleoperation via the Internet,* Proceedings of the IEEE International Conference on Robotics and Automation, Apr. 2000, http://goldberg.berkeley.edu/pubs/ctoi.pdf.

Dalton, *Techniques for Web Telerobotics,* PhD Thesis, University of Western Australia, 2001, pp. 27-62, 149-191, http://telerobot.mech.uwa.edu.au/information.html.

Defendant VGo Communications, Inc.'s Invalidity Contentions Pursuant to the Feb. 27, 2012 Civil Minute Order, May 2, 2012.

Defendant-Counterclaimant VGo Communications, Inc.'s Supplemental Invalidity Contentions Pursuant to the Feb. 27, 2012 Civil Minute Order, May 14, 2012.

(56) References Cited

OTHER PUBLICATIONS

Dudenhoeffer et al., and Control Architectures for Autonomous Micro-Robotic Forces, http://www.inl.gov/technicalpublications/Documents/3157051.pdf, Apr. 2001.
Elhajj, *Synchronization and Control of Supermedia Transmission Via the Internet,* Proceedings of 2001 International Symposium of Intelligent Multimedia, Video and Speech Processing, May 2-4, 2001, Hong Kong.
Elhajj, *Real-Time Haptic Feedback in Internet-Based Telerobotic Operation,* IEEE International Conference on Electro/Information Technology, Jun. 2000 http://www.egr.msu.edu/~ralab-web/cgi__bin/internet-teleoperation.php.
Fiorini, *Health Care Robotics: A Progress Report,* Proceedings of the 1997 IEEE International Conference on Robotics and Automation, Apr. 1997, pp. 1271-1276.
Fong, *Collaborative Control: A Robot-Centric Model for Vehicle Teleoperation,* The Robotics Institute Carnegie Mellon University, Nov. 2001 http://web.archive.org/web/20030504040803/www.ricmu.edu/cgi-bin/tech__reports.cgi?year=2001&text=0.
Goldberg, et al., *Desktop Teleoperation via the World Wide Web,* Proceedings of the IEEE International Conference on Robotics and Automation, 1995.
Hanebeck, *ROMAN: A Mobile Robotic Assistant for Indoor Service Applications,* Proceedings of the 1997 IEEE/RSJ International Conference on Intelligent Robots and Systems, 1997.
Handley et al., RFC 2327-SDP: Session Description Protocol, http://www.faqs.org/rfcs/rfc2327.html, Apr. 1998.
Holmberg, et al., *Development of a Holonomic Mobile Robot for Mobile Manipulation Tasks,* International Conference on Field and Service Robotic, Aug. 1999.
ITU-T H.323 *Packet-based Multimedia Communications Systems,* International Telecommunication Union, Feb. 1998 http://www.itu.int/rec/T-RECH.323-199802-S.
ITU, ITU-T H.281—A Far End Camera Control Protocol for Videoconferences using H.224, http://www.itu.int/rec/T-RECH.281-199411-I/en, Nov. 1994.
ITU, ITU H.450.9 Call Completion Supplementary Services for H.323, http://www.itu.int/rec/T-RECH.450.9-200011-I/en, Nov. 2000.
ITU, Call Intrusion Supplementary Service for H.323, http://www.itu.int/rec/T-RECH.450.11-200103-I/en, Mar. 2001.
Jenkins et al., Telehealth Advancing Nursing Practice, Nursing Outlook, Mar. 2001.
Long, *Robot Navigation Technology* (HelpMate Robotics, Inc.) National Institute of Standards and Technology, Advanced Technology Program, Special Publication 950-1, Mar. 1999.
Mair, Telepresence—The Technology and Its Economic and Social Implications, IEEE Technology and Society, 1997.
Meng et al., *E-Service Robot in Home Healthcare,* Proceedings of the 2000 IEEE/RSJ International Conference on Intelligent Robots and Systems, 2000 http://www.mendeley.com/research/eservicerobot-in-homehealthcare/.
Metz, HP Labs, PCMAG.com, http://www.pcmag.com/article2/0,2817,1130820,00.asp, Jul. 1, 2003.
Michaud, *Introducing 'Nursebot',* The Boston Globe, Sep. 11, 2001, p. F5 http://www.cs.cmu.edu/~nursebot/web/press/globe__3__01/index.html.
Oh, et al., *Autonomous Battery Recharging for Indoor Mobile Robots,* Proceedings of Australian Conference on Robotics and Automation, 2000.
Paulos, *Designing Personal Teleembodiment,* IEEE International Conference on Robotics and Automation, 1998.
Paulos, *Personal Tele-embodiment,* PhD Dissertation, University of California at Berkeley, 2001http://www.paulos.net/papers/dissertation/Eric%20Paulos%20PhD%20Dissertation.pdf.
Paulos, *PRoP: Personal Roving Presence,* ACM-CHI Proceedings, 1998, http://www.paulos.net/papers/1998/chi98.pdf.
Picturetel, PictureTel Live200 for Windows NT Product Guide, http://support.polycom.com/global/documents/support/user/products/video/live200__live200NT__product__guide.pdf, Nov. 1994.
Roach, Automatic Call Back Service in SIP, http://tools.ietf.org/pdf/draftroach-sip-acb-00.pdf, Mar. 2000.
Schulz, et al., *Web Interfaces for Mobile Robots in Public Places,* Robotics and Automation Magazine, vol. 7, Issue 1, Mar. 2000 http://citeseer.ist.psu.edu/cache/papers/cs/32860/http:zSzzSzwww.informatik.unifreiburg.dezSz~burgardzSzabstractsSz..zSzpostscriptszSzwebram00.pdf/schulz99web.pdf.
Simmons, et al., *Xavier: An Autonomous Mobile Robot on the Web,* IEEE Robotics and Automation Magazine, 1999.
Summers, Microsoft NetMeeting 3 Features excerpt from Official Microsoft NetMeeting 3.0 Book, http://technet.microsoft.com/en-us/library/cc723477.aspx#XSLTsection121121120120, excerpt from Microsoft Press http://www.computerbooksonline.com/abook.asp?i=0735605823, Mar. 1999.
Tzafestas et al., *VR-based Teleoperation of a Mobile Robotic Assistant: Progress Report,* Institute of Informatics and Telecommunications, National Center for Scientific Research "Demokritos", DEMO 2000/13, Nov. 2000, pp. 1-23 http://users.softlab.ece.ntua.gr/~ktzaf/Publications/KTzaf__Demo__2000__13.pdf.
West, et al., *Design of Ball Wheel Mechanisms for Omnidirectional Vehicles with Full Mobility and Invariant Kinematics,* Journal of Mechanical Design, vol. 119, Jun. 1997, pp. 153-161.
Zambroski, CMU, Pitt Developing 'nursebot', http://www.cs.cmu.edu/~nursebot/web/press/tribunereview.html, Oct. 27, 2000.
Zamrazil, *Telemedicine in Texas: Public Policy Concerns,* House Research Organization Focus Report, Texas House of Representatives, No. 76-22, May 5, 2000, http://www.hro.house.state.tx.us/focus/telemed.pdf.
Applebome, "Planning Domesticated Robots for Tomorrow's Household", New York Times, http://www.theoldrobots.com/images17/dc17.JPG, Mar. 4,1982, pp. 21,23.
Blackwell, "Video: A Wireless LAN Killer App?", Internet, Apr. 16, 2002, pp. 1-3.
Blaer, et al., "TopBot: Automated Network Topology Detection With a Mobile Robot", Proceedings of the 2003 IEEE International Conference on Robotics 7 Automation, Taipei, Taiwan, Sep. 14-19, 2003, pp. 1582-1587.
Breslow, et al., "Effect of a multiple-site intensive care unit telemedicine program on clinical and economic outcome An alternative paradigm for intensivist staffing", Critical Care Med; vol. 32 No. 1, Jan. 2004, pp. 31-38.
Candelas, et al., "Flexible virtual and remote laboratory for teaching Robotics", FORMATEX 2006; Proc. Advance in Control Education Madrid, Spain, Jun. 2006, pp. 21- 23.
Cheetham, et al., "Interface Development for a Child's Video Conferencing Robot", 2000, pp. 1-4.
Crowley, "Hello to Our Future", AARP Bulletin, http://www.cs.cmu.ed/-nursebot/web/press/aarp 99__14/millennium.html, Jan. 2000.
Dario, "A Robot Workstation for Diagnosis and Physical Therapy", IEEE Catalog No. 88TH0234-5, 1989, pp. 67-72.
Digiorgio, "Is Your Emergency Department of the Leading Edge?", Internet, 2005, pp. 1-4.
Hameed, et al., "A Review of Telemedicine", Journal of Telemedicine and Telecare., vol. 5, Supplement 1, 1999, pp. S1:103-S1:106.
Ivanova, Master's thesis: Internet Based Interface for Control of a Mobile Robot, Department of Numerical Analysis and Computer Science, 2003, 59 pgs.
Johanson, "Supporting video-mediated communication over the Internet", Chalmers University of Technology,Dept of Computer Engineering, Gothenburg, Sweden, 2003.
Keller, et al., "Raven Interface Project", Fall 2001, http://upclose.lrdc.pitt.edu/people/louw__assets/Raven__Slides.pps , Fall 2001.
Linebarger, et al., "Concurrency Control Mechanisms for Closely Coupled Collaboration in Multithreaded Virtual Environments", Presence, Special Issue on Advances in Collaborative VEs, 2004.
Luna, "Robot a new face on geriatric care", OC Register, Aug. 6, 2003.
Martin, "Days Ahead", Assisted Living Today, vol. 9, Nov./Dec. 2002, pp. 19-22.
Motorola Technical Developments, et al., "Detection of Target Mobile Signal Strength", PriorArt Database: Technical Disclosure, IP.com, Retrieved from http:www.ip.com/pubview/

(56) References Cited

OTHER PUBLICATIONS

IPCOM000009024D, original publication date: Jan. 1, 1999 by Motorola, Inc., pp. 205-206, Aug. 1, 2002, pp. 1583-1587.
National Energy RES SCI COMP CTR, "Berkeley Lab's Rage Telepresence Robot Captures R&D100 Award", http://www.nersc.gov/news/newsroom/RAGE070202.php, Jul. 2, 2002.
Noritsugu, "Application of Rubber Artificial Muscle Manipulator as a Rehabilitation Robot", IEEE/ASME Transations on Mechatronics, vol. 2, No. 4, Dec. 1997, pp. 259-267.
Ogata, et al., "Emotional Communication Robot: WAMOEBA-2R-Emotion Model and Evaluation Experiments", Internet, 1999, pp. 1-16.
Spawar Systems Center, "Robart", San Diego, CA, http://www.nosc.mil/robots/land/robart/robart.html, 1998, pp. 1-8.
Stephenson, "Dr. Robot Tested at Hopkins", Internet, Aug. 5, 2003, pp. 1-2.
Tahboub, et al., "Dynamics Analysis and Control of a Holonomic Vehicle With Continously Variable Transmission", Journal of Dynamic Systems, Measurement and Control ASME vol. 124, Mar. 2002, pp. 118-126.
Urquhart, "InTouch's robotic Companion 'beams up' healthcare experts", Medical Device Daily, vol. 7, No. 39, Feb. 27, 2003, pp. 1,4.
Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Adams, Chris, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.
Android Amusement Corp., "What Marketing Secret . . . Renting Robots from Android Amusement Corp!", (Advertisement), 1982.
Applebome, "Planning Domesticated Robots for Tomorrow's Household", New York Times, http://www.theoldrobots.com/images17/dc17.JPG, Mar. 4, 1982, pp. 21,23.
Bartholomew, "An Apothecary's Pharmacy", http://classes.bnf.fr/ema/grands/034.htm, National Library of France, BnF-Teaching Kit-Childhood in the Middle Ages, Encyclopedic reference entry from Bartholomew of England, Book of the Properties of Things, France, Late XVth Century Paris, BnF, Manuscripts Department, 218 French, fol. 111, no date.
Bauer, Jeffrey C. et al., "Service Robots in Health Care: The Evolution of Mechanical Solutions to Human Resource Problems", Jun. 2003.
Bauer, John et al., "Remote telesurgical mentoring: feasibility and efficacy", IEEE, 2000, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Internet, Apr. 16, 2002 pp. 1-3.
Breslow, Michael J. et al., "Effect of a multiple-site intensive care unit telemedicine program on clinical and economic outcome An alternative paradigm for intensivist staffing", Critical Care Med; vol. 32 No. 1, Jan. 2004, pp. 31-38.
Brooks, Rodney, "Remote Presence", Abstracts from Flesh & Machines, How Robots Will Change Us, Feb. 2002, pp. 131-147.
Candelas, Herias et al., "Flexible virtual and remote laboratory for teaching Robotics", FORMATEX 2006; Proc. Advance in Control Education Madrid, Spain, Jun. 2006, pp. 21-23.
Celi, et al., "The EICU: It's not just telemedicine", Critical Care Medicine vol. 29, No. 8 (Supplement), Aug. 2011.
Cheetham, Anastasia et al., "Interface Development for a Child's Video Conferenecing Robot", 2000, pp. 1-4.
CNN.COM/TECHNOLOGY, "Paging R.Robot: Machine helps doctors with patients", Internet, Sep. 30, 2003, pp. 1-3.
Crowley, Susan L., "Hello to Our Future", AARP Bulletin, http://www.cs.cmu.ed/-nursebot/web/press/aarp 99_14/millennium.html, Jan. 2000.
Davies, Brian, "Robotics in Minimally Invasive Surgery", Mechatronics in Medicine Lab, Dept Mechanical Engineering, Imperial College, London SW7 2BX, The Institution of Electrical Engineers, IEE, Savoy Place, London WC2R OBL, UK, 1995, pp. 5/1-5/2.
Digiorgio, James, "Is Your Emergency Department of the Leading Edge?", Internet, 2005, pp. 1-4.
Discovery Channel Canada, "Inventing the Future: 2000 Years of Discovery", http://www.sfwriter.com/pritf.htm, (Video Transcript), Jan. 2, 2000.
Ellison, et al., "Telerounding and Patient Satisfaction Following Surgery", pp. 523-530.
Fels, "Developing a Video-Mediated Communication System for Hospitalized Children", Telemedicine Journal, vol. 5, No. 2, 1999.
Fetterman, "Videoconferencing over the Internet", Internet, 2001, pp. 1-8.
Ghiasi, et al., "A Generic Web-based Teleoperations Architecture: Details and Experience", SPIE Conference on Telemanipulator and Telepresence Technologies VI, Sep. 1999.
Goldberg, "More Online Robots: Robots that Manipulate", Internet Robots, Updated Aug. 2001, http://ford.ieor.berkeley.edu/ir/robots_a2.html, Aug. 2001, pp. 1-3.
Goldenberg, et al., "Telemedicine in Otolaryngology", American Journal of Otolaryngology vol. 23,No. 1, 2002 , pp. 35-43.
Goldman, Lea , "Machine Dreams", Entrepreneurs, Forbes, May 27, 2002.
Gump, Michael D., "Robot Technology Improves VA Pharmacies", Internet, 2001, pp. 1-3.
Hameed, Mohammed et al., "A Review of Telemedicine", Journal of Telemedicine and Telecare., vol. 5, Supplement 1, 1999, pp. S1:103-S1:106.
Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Haule, et al., "Control Scheme for Delayed Teleoperation Tasks", Proceedings of the Pacific Rim Conference on Communications, Computer and Signal Processing, May 17, 1995.
Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.
Ivanova, Natal!, "Master's thesis: Internet Based Interface for Control of a Mobile Robot", Department of Numerical Analysis and Computer Science, 2003, 59 pgs.
Johanson, "Supporting video-mediated communication over the Internet", Chalmers University of Technology, Dept of Computer Engineering, Gothenburg, Sweden, 2003.
Jouppi, Norman et al., "First Steps Towards Mutually-Immersive Mobile Telepresence", CSCW, 02, New Orleans LA, Nov. 16-20, 2002.
Kanehiro, Fumio et al., "Virtual Humanoid Robot Platform to Develop Controllers of Real Humanoid Robots without Porting", IEEE, 2001, pp. 3217-3276.
Kaplan, A. E. et al., "An Internet Accessible Telepresence", {aek keshav nls jhv}@research.att.com, AT&T Bell Laboratories, Murray Hill, N.J., pp. 1-7.
Keller, et al., "Raven Interface Project", Fall 2001, http://upclose.lrdc.pitt.edu/people/louw_assets/Raven_Slides.pps, Fall 2001.
Khatib, "Robots in Human Environments", Proc. International Conference on Control, Automation, Robotics, and Vision ICRACV2000, Singapore, Dec. 2000, pp. 454-457.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Kuzuoka, et al., "Can the GestureCam Be a Surrogate?", Proceedings of the Fourth European Conference on Computer-Supported Cooperative Work, Sep. 10-14, pp. 181-196.
Lane, "Automated Aides", Newsday, http://www.cs.cum.edu/nursebot/web/press/nd4380.htm, Oct. 17, 2000.
Lee, et al., "A novel method of surgical instruction: International telementoring", Internet, 1998, pp. 1-4.

(56) References Cited

OTHER PUBLICATIONS

Lim, Hun-Ok et al., "Control to Realize Human-like Walking of a Biped Humanoid Robot", IEEE, 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs, 2004.
Luna, Nancy, "Robot a new face on geriatric care", OC Register, Aug. 6, 2003.
Martin, Anya, "Days Ahead", Assisted Living Today, vol. 9, Nov./Dec. 2002, pp. 19-22.
Montemerlo, "Telepresence: Experiments in Next Generation Internet", CMU Robotics Institute, http://www.ri.cmu.edu/creative/archives.htm (Video/Transcript), Oct. 20, 1998.
Murphy, "Introduction to A1 Robotics", A Bradford Book, 2000, p. 487.
Nomadic Technologies Inc., "Nomad XR4000 Hardware Manual", Release 1.0, Mar. 1999.
Nt'l Energy RES SCI COMP CTR, "Berkeley Lab's Rage Telepresence Robot Captures R&D100 Award", http://www.nersc.gov/news/newsroom/RAGE070202.php, Jul. 2, 2002.
Ogata, et al., "Emotional Communication Robot: Wamoeba-2R—Emotion Model and Evaluation Experiments", Internet, 1999, pp. 1-16.
Ohja, A. K., "An application of Virtual Reality in Rehabilitation", IEEE, Apr. 10-13, 1994, pp. 4-6.
Paulos, et al., "A World Wide Web Telerobotic Remote Environment Browser", http://vive.cs.berkeley.edu.capek, 1995.
Paulos, "Video of PRoP 2 at Richmond Field Station", www.prop.org Printout of Home Page of Website and two-page Transcript of the audio portion of said PRoP Video, May 2001.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, http://morpha.de/download/publications/IPA, 1999.
Siegwart, "Interacting Mobile Robots on the Web", Proceedings of the 1999 IEEE International Conference on Robotics and Automation, May 1999.
Spawar Systems Center, "Robart", San Diego, CA, http://www.nosc.mil.robots/land/robart/robart.html, 1998, pp. 1-8.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Suplee, "Mastering the Robot", The Washington Post, http://www.cs.cmu.edu-nursebotlweb/press/wash/index.html, Sep. 17, 2000, p. A01.
Tahboub, Karim A. et al., "Dynamics Analysis and Control of a Holonomic Vehicle With Continously Variable Transmission", Journal of Dynamic Systems, Measurement and Control ASME vol. 124, Mar. 2002, pp. 118-126.
Thrun, et al., "Probabilistic Algorithms and the Interactive Museum Tour-Guide Robot Minerva", Internet, 2000, pp. 1-35.
Urquhart, Kim, "InTouch's robotic Companion 'beams up' healthcare experts", Medical Device Daily, vol. 7, No. 39, Feb. 27, 2003, pp. 1,4.
Weiss, et al., "Telework and video-mediated communication: Importance of real-time, interactive communication for workers with disabilities", California State University Northridge http://www.csun.edu/cod/conf/1999/proceedings/session0238.html, pp. 1-4.
Weiss, Patrice L. et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zipperer, Lorri, "Robotic dispensing system", ISMP Medication Safety Alert! vol. 4, Issue 17, Aug. 25, 1999, pp. 1-2.
Zorn, Benjamin G., "Ubiquitous Telepresence", http://www.cs.colorado.edu/-zorn/ultvision/vision.html, Mar. 3, 1996.
Adams, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.
Ando, et al., "A Multimedia Self-service Terminal with Conferencing Functions", IEEE, Jul. 5-7, 1995, pp. 357-362.
Bar-Cohen, et al., "Virtual reality robotic telesurgery simulations using MEMICA haptic system", Internet, Mar. 5, 2001, pp. 1-7.
Bauer, et al., "Service Robots in Health Care: The Evolution of Mechanical Solutions to Human Resource Problems", Jun. 2003.
Bauer, et al., "Remote telesurgical mentoring: feasibility and efficacy", IEEE, 2000, pp. 1-9.
Brooks, "Remote Presence", Abstracts from Flesh & Machines, How Robots Will Change Us, Feb. 2002, pp. 131-147.
Celt, et al., "The EICU: It's not just telemedicine", Critical Care Medicine vol. 29, No. 8 (Supplement), Aug. 2001.
Cleary, et al., "State of the art in surgical robotics: Clinical applications and technology challenges", Internet, Feb. 24, 2002, pp. 1-26.
CNN, "Floating 'droids' to roam space corridors of the future", Internet, Jan. 12, 2000, pp. 1-4.
Davies, "Robotics in Minimally Invasive Surgery", Mechatronics in Medicine Lab, Dept Mechanical Engineering, Imperial College, London SW7 2BX, The Institution of Electrical Engineers, IEE, Savoy Place, London WC2R OBL, UK, 1995, pp. 5/1-5/2.
Elhajj, et al., "Supermedia in Internet-based telerobotic operations", Internet, 2001, pp. 1-14.
Ellison, et al., "Telerounding and Patient Satisfaction Following Surgery", pp. 523-530, (2004).
Goldberg, et al., "Collaborative Teleoperation via the Internet", IEEE International Conference on Robotics and Automation, San Francisco, California, Apr. 2000.
Goldman, "Machine Dreams", Entrepreneurs, Forbes, May 27, 2002.
Gump, "Robot Technology Improves VA Pharmacies", Internet, 2001, pp. 1-3.
Harmo, et al., "Moving Eye-Interactive Telepresence Over Internet With a Ball Shaped Mobile Robot", 2000.
Hees, "Communications Design for a Remote Presence Robot", Jan. 14, 2002.
Ishihara, et al., "Intelligent Microrobot DDS (Drug Delivery System) Measured and Controlled by Ultrasonics", IEEE/RSJ, vol. 2, Nov. 3-5, 1991, pp. 1145-115.
Jouppi, et al., "Mutually-Immersive Audio Telepresence", Audio Engineering Society Convention Paper presented at 113th Convention, Oct. 2002.
Jouppi, et al., "First Steps Towards Mutually-Immersive Mobile Telepresence", CSCW, 02, New Orleans LA, Nov. 16-20, 2002.
Kanehiro, et al., "Virtual Humanoid Robot Platform to Develop Controllers of Real Humanoid Robots without Porting", IEEE, 2001, pp. 3217-3276.
Kaplan, et al., "An Internet Accessible Telepresence", {aek keshav nls jhv}@research.att.com, AT&T Bell Laboratories, Murray Hill, N.J., pp. 1-7, (1996).
Kuzuoka, et al., "Can the GestureCam Be a Surrogate?", Proceedings of the Fourth European Conference on Computer-Supported Cooperative Work, Sep. 10-14, pp. 181-196, (1995).
Lim, et al., "Control to Realize Human-like Walking of a Biped Humanoid Robot", IEEE, 2000, pp. 3271-3276.
Loeb, et al., "Virtual Visit: Improving Communication for Those Who Need It Most", Stud Health Technol Inform.; 94: 302-8., 2003.

(56) References Cited

OTHER PUBLICATIONS

Mack, "Minimally invasive and robotic surgery", Internet IEEE, 2001, pp. 568-572.
McCardle, et al., "The challenge of utilizing new technology in design education", Internet, 2000, pp. 122-127.
Nakajima, et al., "A Multimedia Teleteaching System using an Electronic Whiteboard for Two Way Communication of Motion Videos and Chalkboards", IEEE, 1993, pp. 436-441.
Ogata, et al., "Development of Emotional Communication Robot: WAMOEBA-2r—Experimental Evaluation", IEEE, 2000, pp. 175-180.
Ojha, "An application of Virtual Reality in Rehabilitation", IEEE, Apr. 10-13, 1994, pp. 4-6.
Paulos, et al., "A World Wide Web Telerobotic Remote Environment Browser", http://vive.cs.berkeley.edu/capek, 1995.
Paulos, et al., "Ubiquitous Tele-embodiment: Applications and Implications", International Journal of Human Computer Studies, vol. 46, No. 6, Jun. 1997, pp. 861-877.
Pin, et al., "A New Family of Omnidirectional and Holonomic Wheeled Platforms for Mobile Robots", IEEE, vol. 10, No. 4, Aug. 1994.
Sandt, et al., "Perceptions for a Transport Robot in Public Environments", IROS, 1997.
Shimoga, et al., "Touch and force reflection for telepresence surgery", IEEE, 1994, pp. 1049-1050.
Tendick, et al., "Human-Machine Interfaces for Minimally Invasive Surgery", IEEE, 1997, pp. 2771-2776.
Weiss, et al., "Telework and video-mediated communication: Importance of real-time, interactive communication for workers with disabilities", California State University Northridge http://www.csun.edu/cod/conf/1999/proceedings/session0238.html, pp. 1-4, (1999).
Weaver; Monitoring and Control Using the Internet and Java; Copyright 1999; 7 pages.
Leifer; VIPRR: A Virtually in Person Rehabilitation Robot; Aug. 3, 2012; http://www.standrod.edu/group/rrd/People/vdl/publications/ICORR97/VIPRR.html; 4 pages.
Garner; The Application of Telepresence in Medicine; Jan. 22, 2014; http://link.springer.com/article/10.
1023%2FA%3A1018699900499; 4 pages.
Pioneer 2 / PeopleBot Operations Manual; Copyright 2001; ActivMedia Robotics, LLC; 78 pages.
ActivMedia, Saphira Software Manual; Copyright 1997; 105 pages.
Christensen; BeeSoft User's Guide and Reference; Copyright 1997; 203 pages.
PictureTel Adds New Features and Functionality to Its Award-Winning Live 200 Desktop Videoconferencing System; Jun. 13, 1997; 5 pages.
Webpage print out of www.ri.cmu.deu/publications_view.html?pubid=3826, entitled Robotics Institute: Web interfaces for mobile robots in public places; Mar. 2000, 3 pages.
U.S. Appl. No. 60/449,762, filed Feb. 24, 2003; 28 pages.
U.S. Appl. No. 10/783,760, filed Feb. 20, 2004; 48 pages.
Thrun et al; Probalistic Algorithms and the Interactive Museum Tour-Guide Robot Minerva; Nov. 2000, pp. 972-999.
Brooks; A Robust Layered Control System for a Mobile Robot; Mar. 1986; 10 pages.
Dean et al.; 1992 AAAI Robot Exhibition and Competition; Spring 1993; 15 pages.
Office Coworker Robot; Time Magazine; Nov. 2001; 2 pages.
Wired, Telefriend, Meet iRobot, the smartest webcam on wheels; 1994; 3 pages.
Bauer et al., Remote telesurgical mentoring: feasibility and efficacy, 2000, IEEE, p. 1-9.*
Salemi et al., MILO: personal robot platform, 2005, IEEE, p. 4089-4094.*
Johns Hopkins Medical Institutionsl Stephenson, Dr. Robot Tested at Hopkins, 2003, Internet, p. 1-2.*
F. Ando et al., "A Multimedia Self-service Terminal with Conferencing Functions", 1995, IEEE, pp. 357-362.
Bar-Cohen et al., Virtual reality robotic telesurgery simulations using MEMICA haptic system, Mar. 5, 2001, Internet, pp. 1-7.
Bauer, John et al., "Remote telesurgical mentoring: feasibility and efficacy", 2000, IEEE, pp. 1-9.
Brooks, Rodney, Abstracts from Flesh & Machines, How Robots Will Change Us, "Remote Presence", p. 131-147, Feb. 2002.
Celi et al., "The eICU: It's not just telemedicine", Critical Care Medicine, vol. 29, No. 8 (Supplement), Aug. 2001.
Cleary et al., "State of the art in surgical robotics: Clinical applications and technology challenges", Feb. 24, 2002, Internet, pp. 1-26.
CNN, Floating 'droids' to roam space corridors of the future, Jan. 12, 2000, Internet, pp. 1-4.
Davies, "Robotics in Minimally Invasive Surgery", 1995, Internet, pp. 5/1-5/2.
Elhajj et al., "Supermedia in Internet-based telerobotic operations", 2001, Internet, pp. 1-14.
Goldberg et al., "Collaborative Teleoperation via the Internet", IEEE International Conference on Robotics and Automation, Apr. 2000, San Francisco, California.
Goldman, Lea, "Machine Dreams", Entrepreneurs, Forbes, May 27, 2002.
Gump, Michael D., "Robot Technology Improves VA Pharmacies", 2001, Internet, pp. 1-3.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
Ishihara, Ken et al., "Intelligent Microbot DDS (Drug Deliver System) Measured and Controlled by Ultrasonics", Nov. 3-5, 1991, IEEE/RSJ, pp. 1145-1150, vol. 2.
Kanehiro, Fumio et al., Virtual Humanoid Robot Platform to Develop Controllers of Real Humanoid Robots without Porting, 2001,IEEE, pp. 3217-3276.
Lim, Hun-ok et al., Control to Realize Human-like Walking of a Biped Humanoid Robot, IEE 2000, pp. 3271-3276.
Loeb, Gerald, "Virtual Visit: Improving Communication for Those Who Need It Most", 2001.
Mack, "Minimally invasive and robotic surgery", 2001, Internet IEEE, pp. 568-572.
Magne Charge—Smart Power for Electric Vehicles, Internet, Jun. 27, 2002.
McCardle et al., "The challenge of utilizing new technology in design education", 2000 Internet, pp. 122-127.
Nakajima et al., "A Multimedia Teleteaching System sing an Electronic Whiteboard for Two-Way Communication of Motion Videos and Chalkboards",IEEE , pp. 436-441.
Ogata et al., "Development of Emotional Communication Robot: WAMOEBA-2r—Esperimental evaluation . . . ", 2000 IEEE, pp. 175-180.
Ojha, Anad, "An application of Virtual Reality in Rehabilitation", Jan. 1994, IEEE, pp. 4-6.
Paulos et al., "A World Wide Web Telerobotic Remote Environment Browser", http://vive.cs.berkeley.edu/capek, 1995.
Paulos, Eric John, "Personal Tele-Embodiment", Fall 2001.
Paulos, et al., "Ubiquitous Tele-embodiment: Applications and Implications", International Journal of Human Computer Studies, Jun. 1997, vol. 46, No. 6, pp. 861-877.
Paulos, et al., "Designing Personal Tele-Embodiment", Presented at the IEEE International Conference on Robotics and Animation, Leuven, Belgium, May 20, 1998.
Pin et al., "A New Family of Omnidirectional and Holonomic Wheeled Platforms for Mobile Robots", IEEE, vol. 10, No. 4, Aug. 1994.
Robot Hardware Mobile Robotics Research Group, Edinburgh, "Mobile Robotics Research Group", 2000 Internet, pp. 1-2.
Roy et al., "Towards Personal Service Robots for the Elderly", Internet, Mar. 7, 2002.
Sandt, Frederic et al., "Perceptions for a Transport Robot in Public Environments", 1997, IROS '97.
Shimonga et al., Touch and force reflection for telepresence surgery, 1994, IEEE, pp. 1049-1050.
Tendick et al., "Human-Machine Interfaces for Minimally Invasive Surgery", 1997, IEEE, pp. 2771-2776.

(56) References Cited

OTHER PUBLICATIONS

Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Weiss et al., Telework and video-mediated communication: Importance of real-time, interactive communication for workers with disabilities, 1999, Internet, pp. 1-4.
Yamasaki et al., Applying Personal Robots and Active Interface to Video Conference Systems, 1995, Internet, pp. 243-248.
Yong et al., "Robot task execution with telepresence using virtual reality technology", 1998, Internet, pp. 1-9.
Zipperer, Lorri, "Robotic dispensing system", 1999, Internet, pp. 1-2.
Zorn, Benjamin G., "Ubiquitous Telepresence", http://www.cs.colorado.edu/~zorn/ut/vision.html, Mar. 5, 1996.

* cited by examiner

APPARATUS AND METHOD FOR PATIENT ROUNDING WITH A REMOTE CONTROLLED ROBOT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a continuation of application Ser. No. 10/751,032, filed on Jan. 2, 2004, now U.S. Pat. No. 7,164,969 which is a continuation-in-part of application Ser. No. 10/206,457, filed on Jul. 25, 2002, now U.S. Pat. No. 6,925,357:

BACKGROUND OF THE INVENTION

1. Field of the Invention

The subject matter disclosed generally relates to the field of robotics.

2. Background Information

Patient consultation is a critical component of medical care. For example, it is typically imperative that a physician visit a patient after a surgical procedure. Such visits not only allow the physician to observe the patient for follow-up care, but aids in establishing the all important personal relationship between doctor and patient. Because of various economic and regulatory issues it has become increasing difficult for physicians to develop strong relationships with patients through interactive visits.

John Hopkins Medical Institution has tested a program where tele-conferencing equipment is placed in a patient's room. The doctor can then remotely "visit" the patient through the tele-conferencing system. Such an approach would require tele-conferencing equipment in each patient room, thereby increasing the cost of equipping and maintaining the medical facility. Additionally, the tele-conferencing equipment must be placed in a position to allow the doctor to view the patient. This may be in a location adjacent to the patient's bed. Such a location may not allow the doctor to view an ambulatory patient.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope which has a camera that allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a videoconferencing platform that has both a camera and a monitor. The Treviranus patent also discloses embodiments with a mobile platform, and mechanisms for moving the camera and the monitor.

Publication Application No. US-2003-0050233-A1 discloses a remote robotic system wherein a plurality of remote stations can control a plurality of robotic arms used to perform a minimally invasive medical procedure. Each remote station can receive a video image provided by the endoscope inserted into the patient. The remote stations are linked to the robotic system by a dedicated communication link.

To date there has not been a utilization of mobile robots to allow a doctor to remotely visit a patient. Such a technique would allow more frequent doctor/patient visits and improve the quality of medical care.

BRIEF SUMMARY OF THE INVENTION

A method for remotely monitoring a patient with a robot that has a camera and a microphone. A robot input command is generated and transmitted from a remote station. The robot input command is received by the robot. The robot moves in response to the robot input command. A video image and sound of the patient is transmitted to the remote station from the robot.

DETAILED DESCRIPTION

Disclosed is a method for remotely monitoring a patient. The method includes generating and transmitting input commands to the robot from a remote station. The remote station may include a personal computer that is operated by a doctor. The input commands can move the robot so that a video image and sounds of the patient can be captured by a robot camera and microphone, respectively, and transmitted back to the remote station. The robot may also have a monitor and a speaker to allow for two-way videoconferencing between the patient and a doctor at the remote station. The robot can move from room to room so that a doctor can make "patient rounds" within a medical facility. The system thus allows a doctor to visit patients from a remote location, thereby improving the frequency of visits and the quality of medical care.

Figure 1:
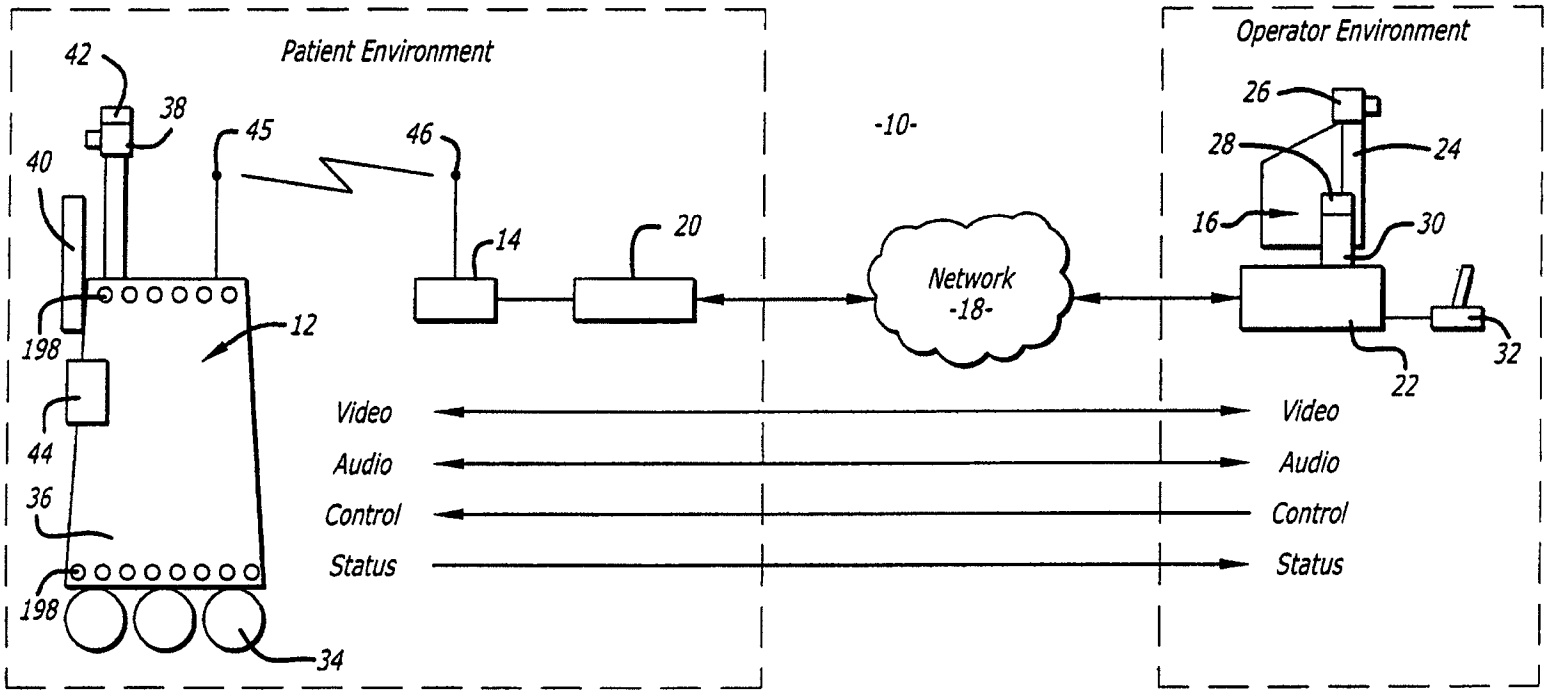
FIG. 1 is an illustration of a robotic system.

Referring to the drawings more particularly by reference numbers, FIG. 1 shows a robotic system 10. The robotic system 10 includes a robot 12, a base station 14 and a remote control station 16. The control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The station 16 is typically located in a place that is remote from the robot 12. Although only one robot 12 is shown, it is to be understood that the system 10 may have a plurality of robots 12. In general any number of robots 12 may be controlled by any number of remote stations. For example, one remote station 16 may be coupled to a plurality of robots 12, or one robot 12 may be coupled to a plurality of remote stations 16.

The robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 may be the same or similar to a robotic system sold by the assignee InTouch-Health, Inc. of Santa Barbara, Calif. under the trademark COMPANION.

Figure 2:
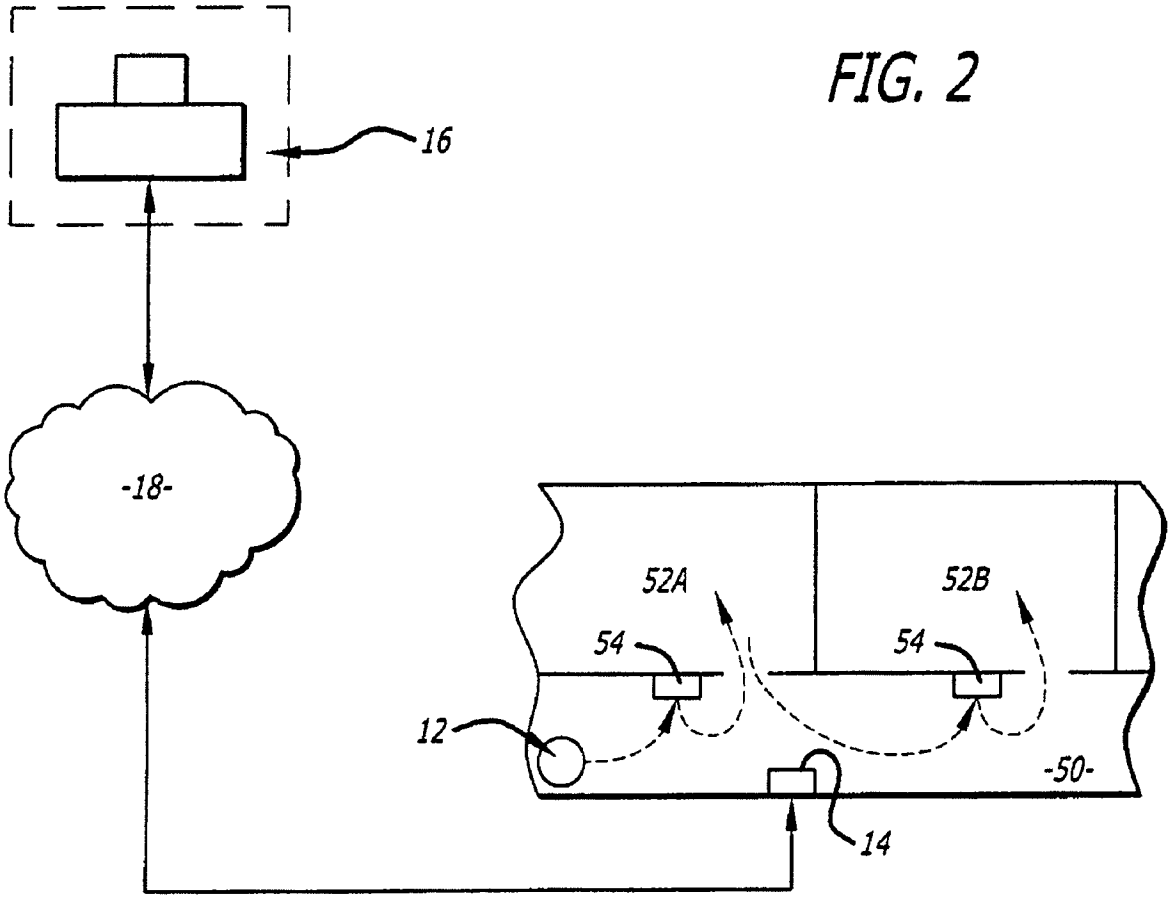
FIG. 2 is a schematic showing movement of a robot in a medical facility.

FIG. 2 shows an implementation of the system in a medical facility 50. The medical facility 50 may be a hospital, assisted living home, etc, that contains a plurality of patient rooms 52, including a first patient room 52A and a second patient room 52B, each containing one or more patients.

A doctor may be located at a remote station 16. The remote station 16 may be on or off the premises of the medical facility 50. The station 16 is linked to the robot 12 by the network 18 and wireless base station 14. The medical facility 50 may have a number of wireless base stations 14 located throughout the facility 50 so that the robot 12 is always linked to a station 14.

The system 10 allows the doctor to make patient rounds in the facility 50. For example, the doctor may generate robot input commands at the remote station 16 that are then transmitted and received by the robot 12. The input commands may cause the robot to move to the door of the first patient room 52A. The doctor can view a chart 54 outside the room through the robot camera. The doctor may utilize a zoom feature of the camera to read the chart.

After reading the chart the doctor may move the robot into the first patient room 52A. The system allows the doctor to conduct a two-way videoconference with the patient. The videoconference may allow the doctor to observe the patient through the robot camera. The doctor can also ask questions that can be generated by the robot speaker and/or displayed by the robot monitor. The robot monitor can display the doctor at the remote station so that the patient feels they are being "visited" by the doctor.

After the visiting the patient in the first patient room 52A the doctor can move the robot 12 to the second patient room 52B where the process is repeated. The system thus allows the doctor to visit multiple patients from a remote location. This increases the frequency of doctor visits, reduces doctor fatigue and improves the overall medical care of the patients.

Figure 3:
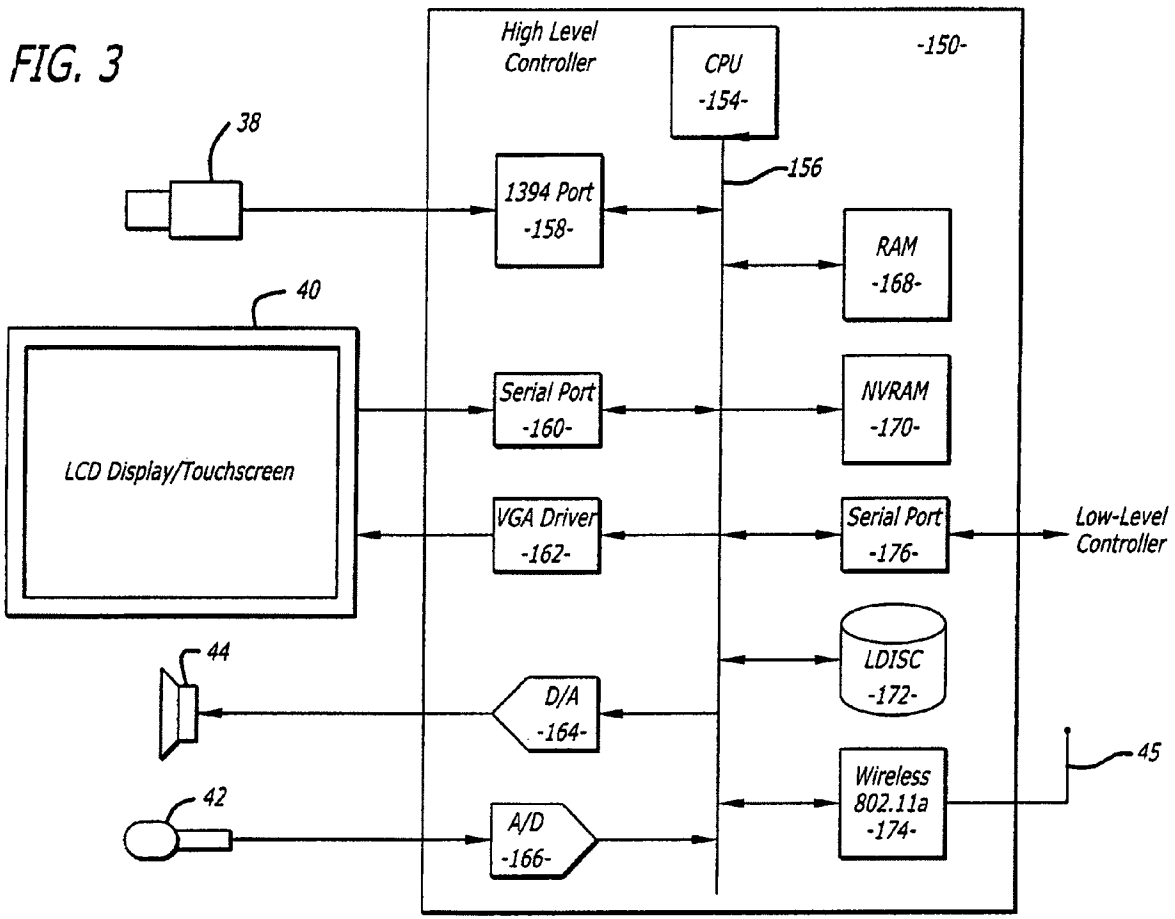
FIG. 3 is a schematic of an electrical system of a robot.
Figure 4:
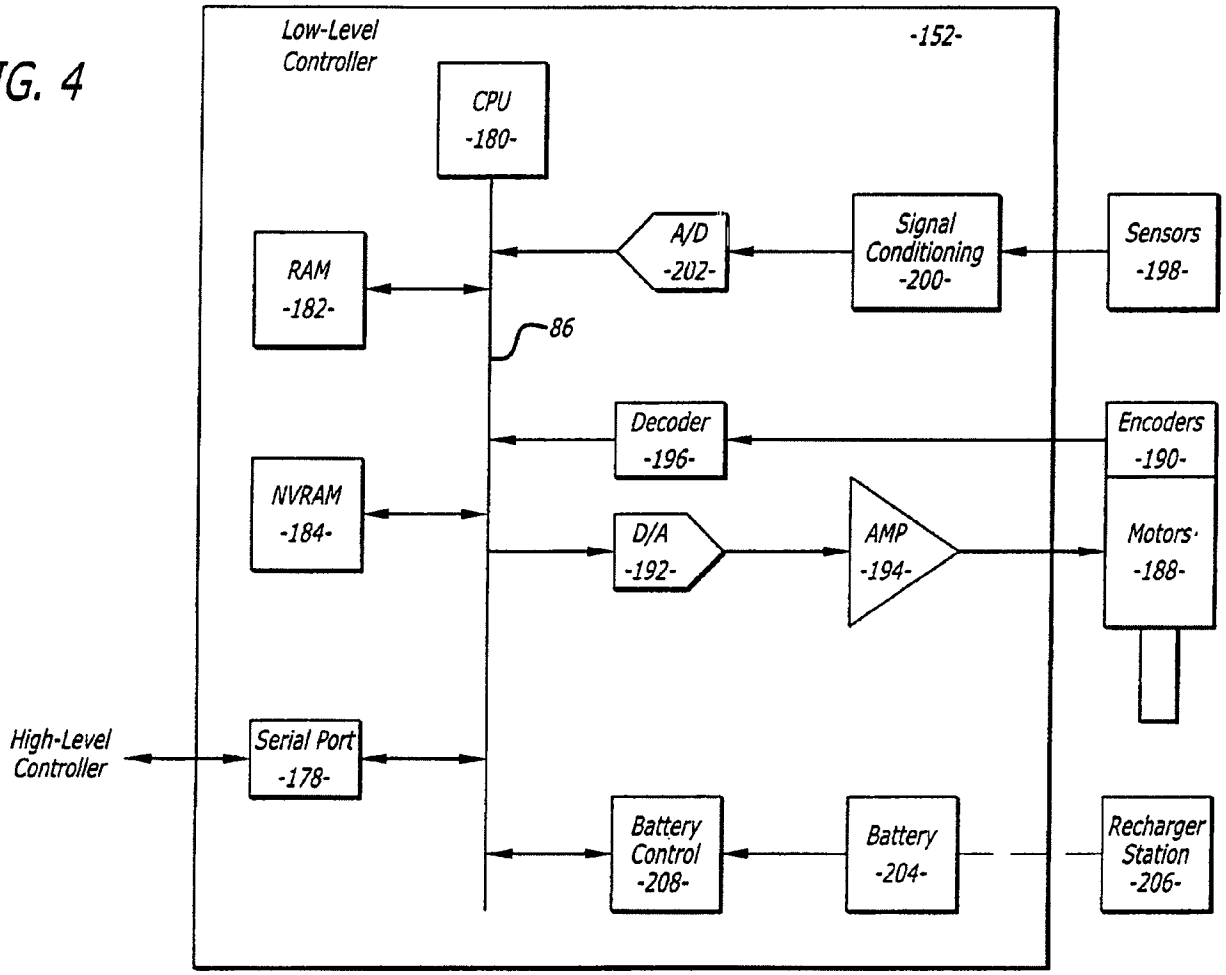
FIG. 4 is a further schematic of the electrical system of the robot.

FIGS. 3 and 4 show an embodiment of the robot 12. The robot 12 may include a high level control system 150 and a low level control system 152. The high level control system 150 may include a processor 154 that is connected to a bus 156. The bus 156 is coupled to the camera 38 by an input/output (I/O) port 158, and to the monitor 40 by a serial output port 160 and a VGA driver 162. The monitor 40 may include a touchscreen function that allows the patient to enter input by touching the monitor screen 40.

The speaker 44 is coupled to the bus 156 by a digital to analog converter 164. The microphone 42 is coupled to the bus 156 by an analog to digital converter 166. The high level controller 150 may also contain random access memory (RAM) device 168, a non-volatile RAM device 170 and a mass storage device 172 that are all coupled to the bus 162. The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 174. By way of example, the transceiver 174 may transmit and receive information in accordance with IEEE 802.11b.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control the communication between the robot 12 and the remote control station 16.

The high level controller 150 may be linked to the low level controller 152 by serial ports 176 and 178. The low level controller 152 includes a processor 180 that is coupled to a RAM device 182 and non-volatile RAM device 184 by a bus 186. The robot 12 contains a plurality of motors 188 and motor encoders 190. The encoders 190 provide feedback information regarding the output of the motors 188. The motors 188 can be coupled to the bus 186 by a digital to analog converter 192 and a driver amplifier 194. The encoders 190 can be coupled to the bus 186 by a decoder 196. The robot 12 also has a number of proximity sensors 198 (see also FIG. 1). The position sensors 198 can be coupled to the bus 186 by a signal conditioning circuit 200 and an analog to digital converter 202.

The low level controller 152 runs software routines that mechanically actuate the robot 12. For example, the low level controller 152 provides instructions to actuate the movement platform to move the robot 12. The low level controller 152 may receive movement instructions from the high level controller 150. The movement instructions may be received as movement commands from the remote control station. Although two controllers are shown, it is to be understood that the robot 12 may have one controller controlling the high and low level functions.

The various electrical devices of the robot 12 may be powered by a battery(ies) 204. The battery 204 may be recharged by a battery recharger station 206 (see also FIG. 1). The low level controller 152 may include a battery control circuit 208 that senses the power level of the battery 204. The low level controller 152 can sense when the power falls below a threshold and then send a message to the high level controller 150. The high level controller 150 may include a power management software routine that causes the robot 12 to move so that the battery 204 is coupled to the recharger 206 when the battery power falls below a threshold value. Alternatively, the user can direct the robot 12 to the battery recharger 206. Additionally, the battery 204 may be replaced or the robot 12 may be coupled to a wall power outlet by an electrical cord (not shown).

Figure 5:
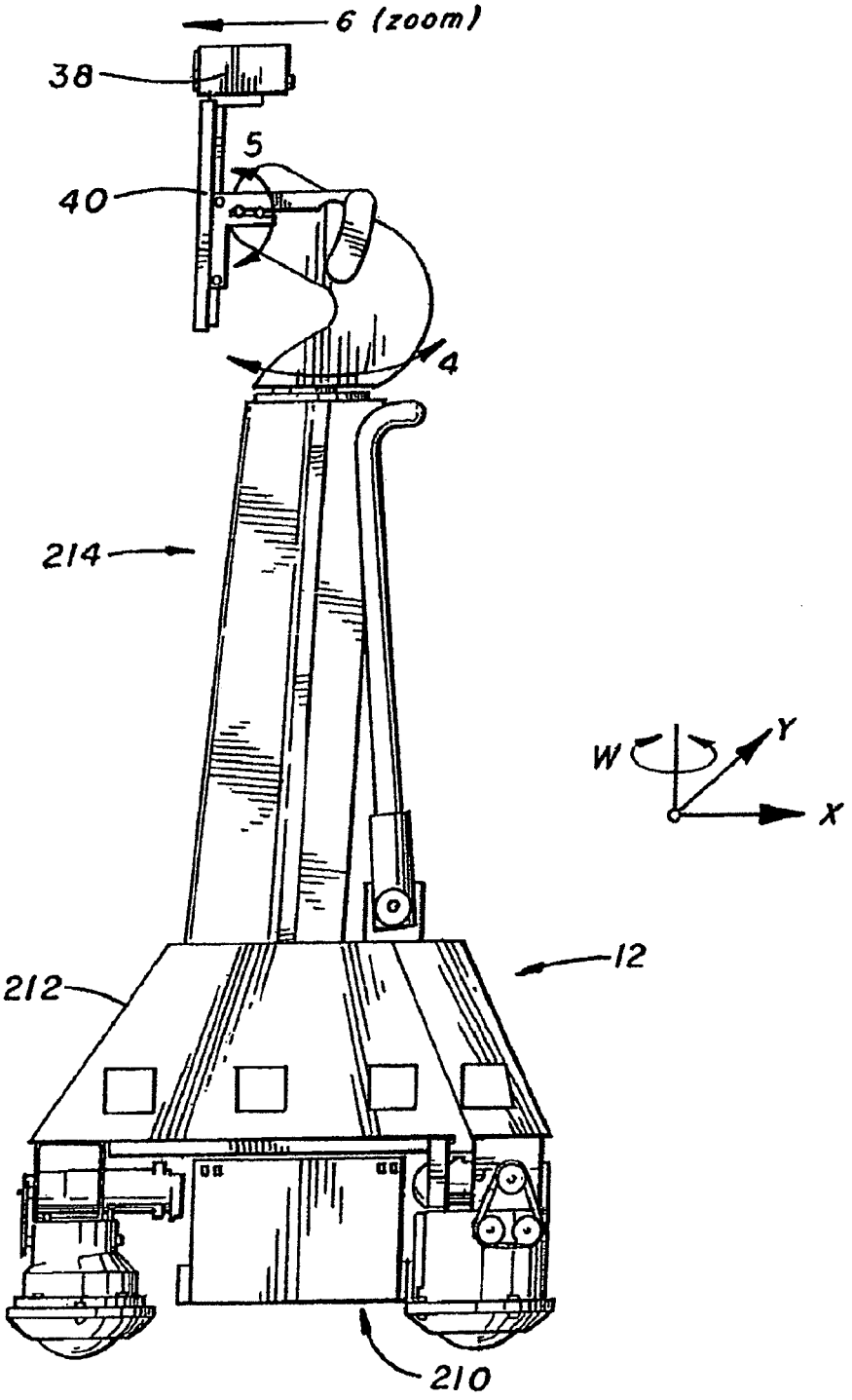
FIG. 5 is side view of the robot.

FIG. 5 shows an embodiment of the robot 12. The robot 12 may include a holonomic platform 210 that is attached to a robot housing 212. The holonomic platform 210 provides three degrees of freedom to allow the robot 12 to move in any direction.

The robot 12 may have a pedestal assembly 214 that supports the camera 38 and the monitor 40. The pedestal assembly 214 may have two degrees of freedom so that the camera 26 and monitor 24 can be swiveled and pivoted as indicated by the arrows.

Figure 6:
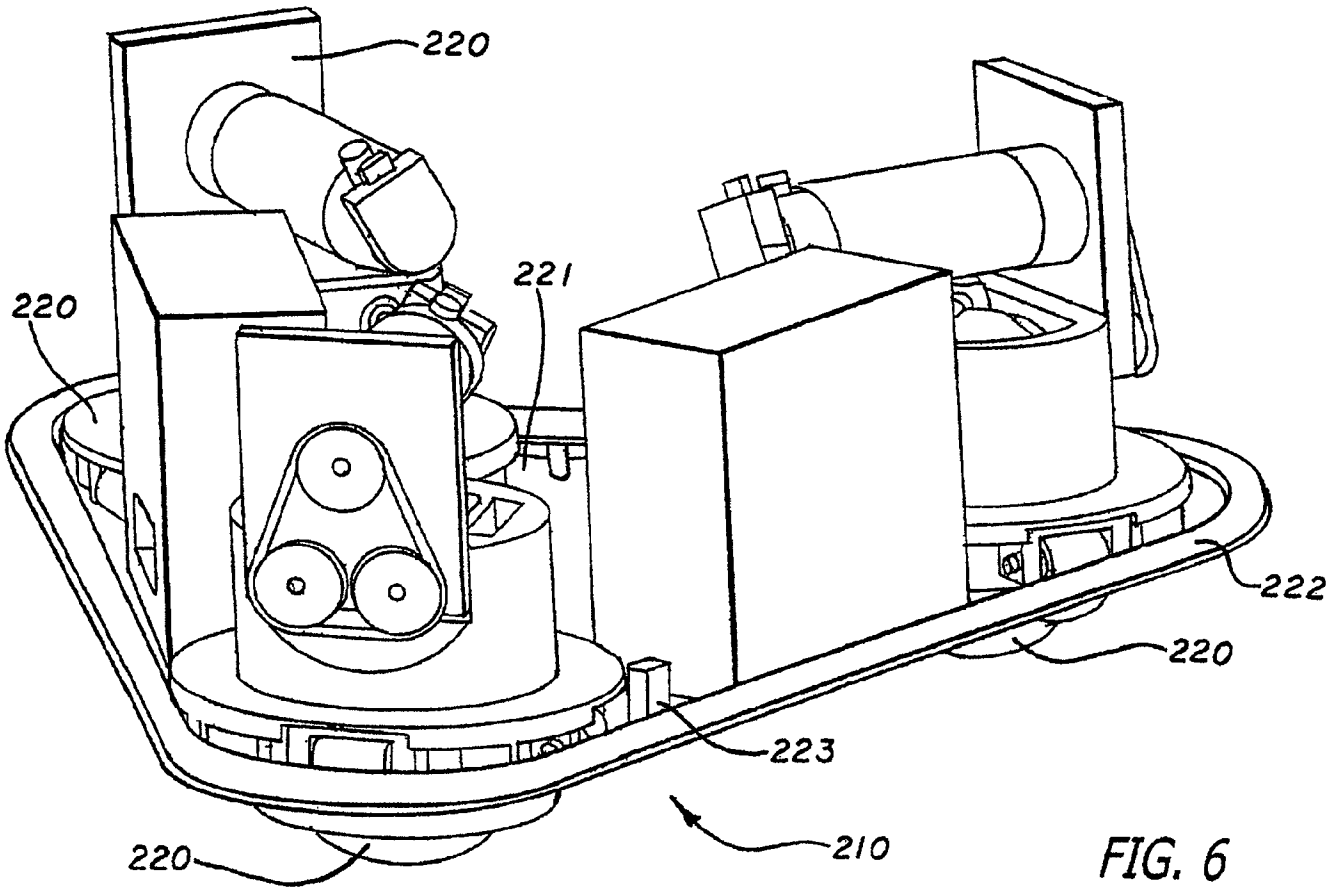
FIG. 6 is a top perspective view of a holonomic platform of the robot.

As shown in FIG. 6 the holonomic platform 210 may include three roller assemblies 220 that are mounted to a base plate 221. The roller assemblies 220 allow for movement in any direction.

The robot housing 212 may include a bumper 222. The bumper 222 may be coupled to optical position sensors 223 that detect when the bumper 222 has engaged an object. After engagement with the object the robot can determine the direction of contact and prevent further movement into the object.

Figure 7:
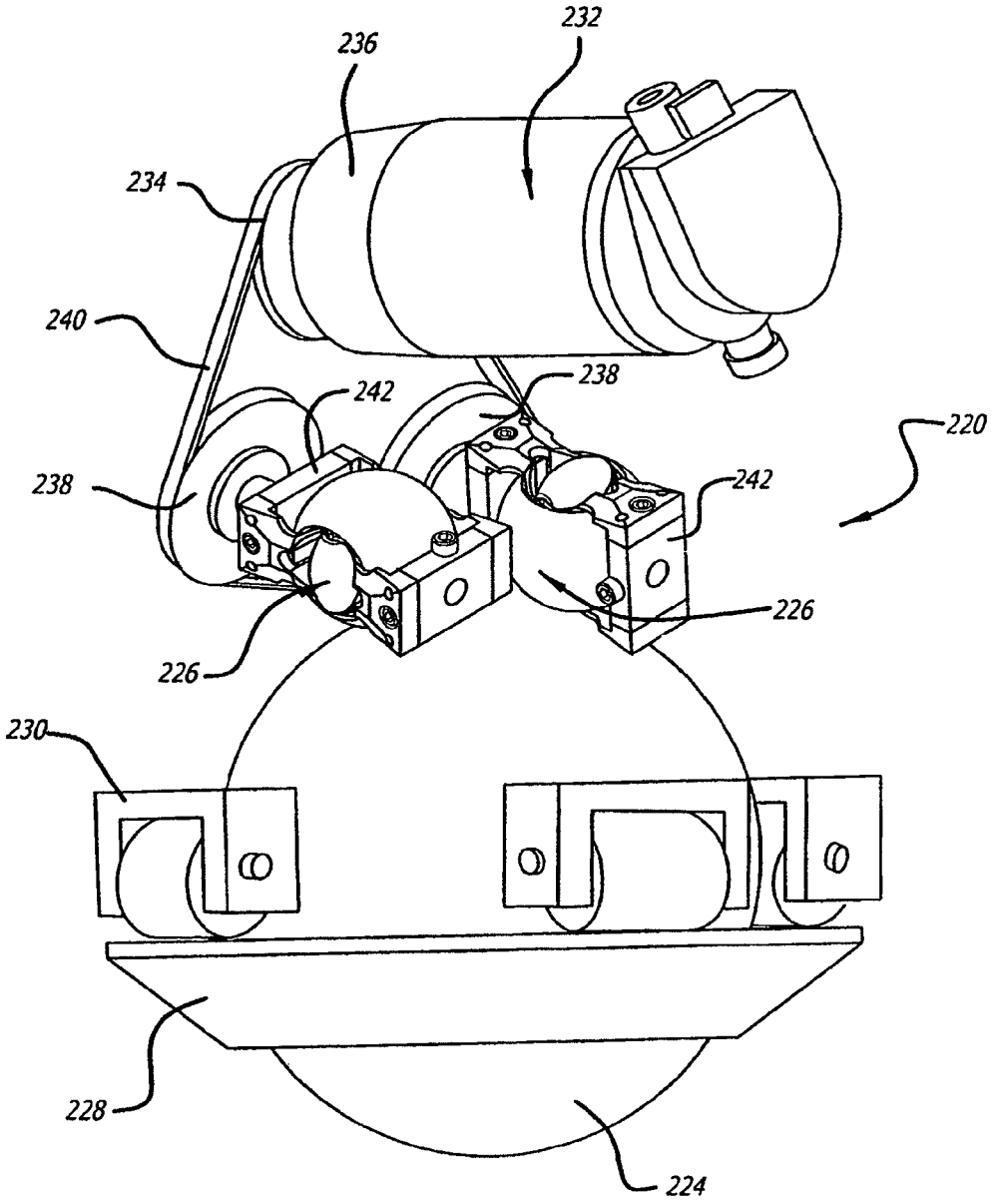
FIG. 7 is aside perspective view of a roller assembly of the holonomic platform.

FIG. 7 shows an embodiment of a roller assembly 220. Each assembly 220 may include a drive ball 224 that is driven by a pair of transmission rollers 226. The assembly 220 may include a retainer ring 228 and a plurality of bushings 230 that capture and allow the ball 224 to rotate in x and y directions but prevent movement in a z direction. The assembly also holds the ball under the transmission rollers 226.

The transmission rollers 226 are coupled to a motor assembly 232. The assembly 232 corresponds to the motor 188 shown in FIG. 4. The motor assembly 232 includes an output pulley 234 attached to a motor 236. The output pulley 234 is coupled to a pair of ball pulleys 238 by a drive belt 240. The ball pulleys 238 are each attached to a transmission bracket 242. The transmission rollers 226 are attached to the transmission brackets 242.

Rotation of the output pulley 234 rotates the ball pulleys 238. Rotation of the ball pulleys 238 causes the transmission rollers 226 to rotate and spin the ball 224 through frictional forces. Spinning the ball 224 will move the robot 12. The transmission rollers 226 are constructed to always be in contact with the drive ball 224. The brackets 242 allow the transmission rollers 226 to freely spin in a direction orthogonal to the driven direction when one of the other roller assemblies 220 is driving and moving the robot 12.

Figure 8:
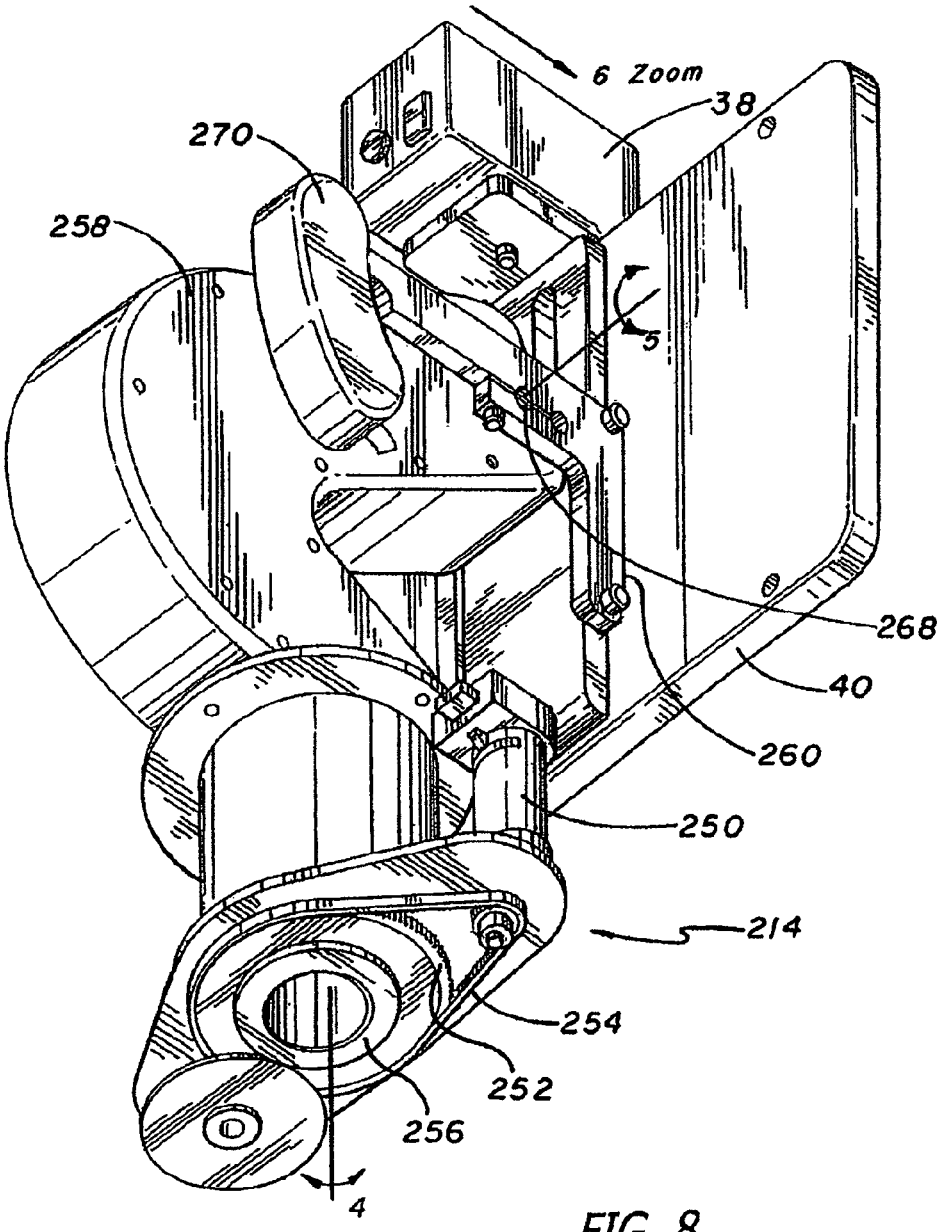
FIG. 8 is a bottom perspective view showing a pedestal assembly of the robot.

As shown in FIG. 8, the pedestal assembly 214 may include a motor 250 that is coupled to a gear 252 by a belt 254. The gear 252 is attached to a shaft 256. The shaft 256 is attached to an arm 258 that is coupled to the camera 38 and monitor 40 by a bracket 260. Activation of the motor 250 rotates the gear 252 and sleeve 256, and causes the camera 38 and monitor 40 to swivel (see also FIG. 5) as indicated by the arrows 4.

Figure 9:
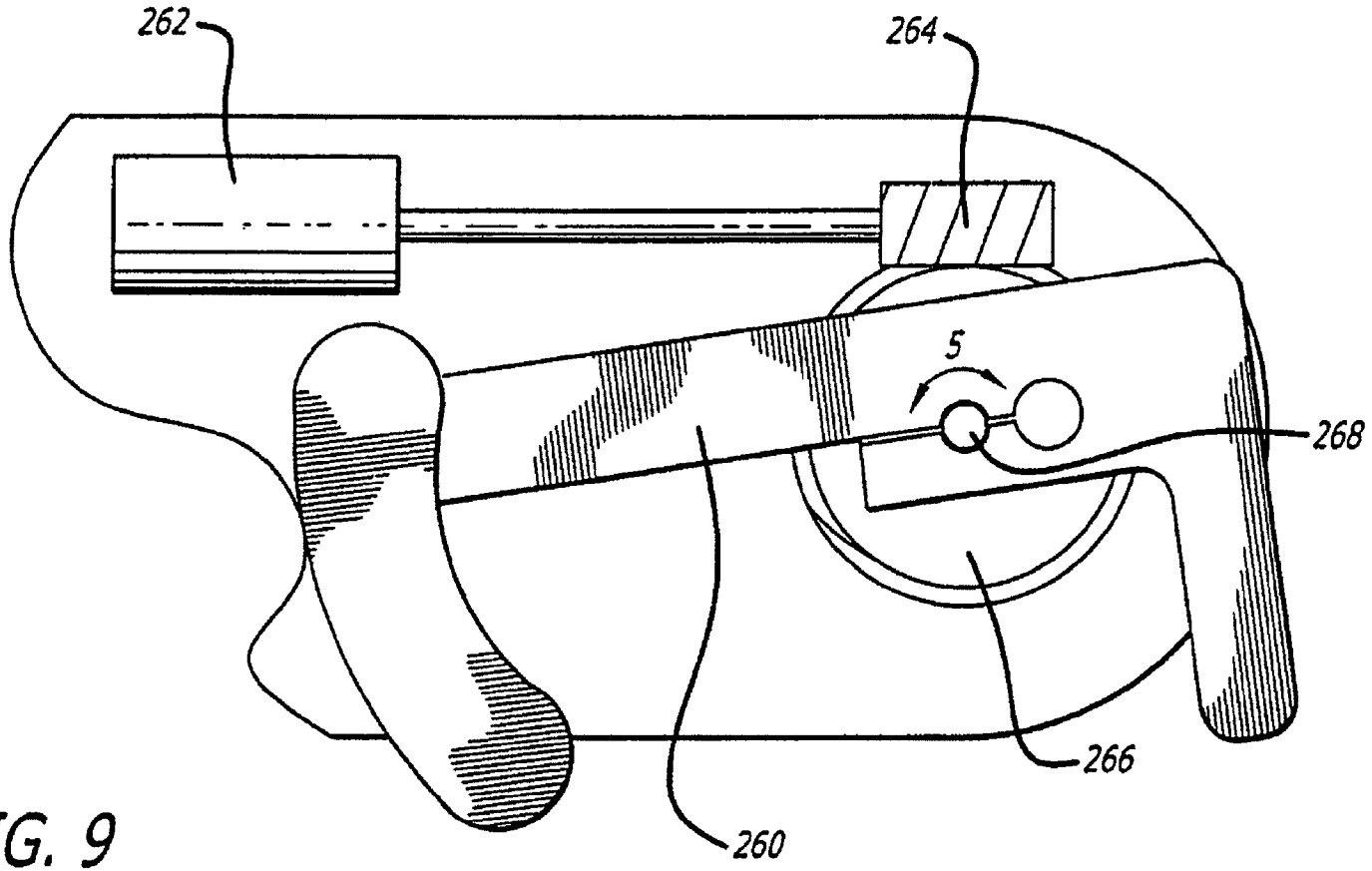
FIG. 9 is a sectional view showing an actuator of the pedestal assembly.

As shown in FIG. 9, the assembly 214 may further include a tilt motor 262 within the arm 258 that can cause the monitor 40 and camera 38 to pivot as indicated by the arrows 5. The tilt motor 262 may rotate a worm 264 that rotates a worm gear 266. The pin 268 is rigidly attached to both the worm gear 266 and the bracket 260 so that rotation of the gear 266 pivots the camera 38 and the monitor 40. The camera 38 may also include a zoom feature to provide yet another degree of freedom for the operator.

The robot 10 may be controlled by a number of different doctors. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |

TABLE I-continued

| User | Access Control | Medical Record | Command Override | Software/Debug Access | Set Priority |
|---|---|---|---|---|---|
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m<br>pending user | Warn current user of pending user<br>Notify requesting user that system is in use<br>Set timeout = 5 m<br>Queue or callback | Warn current user of pending user<br>Notify requesting user that system is in use<br>No timeout<br>Call back |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

Figure 10:
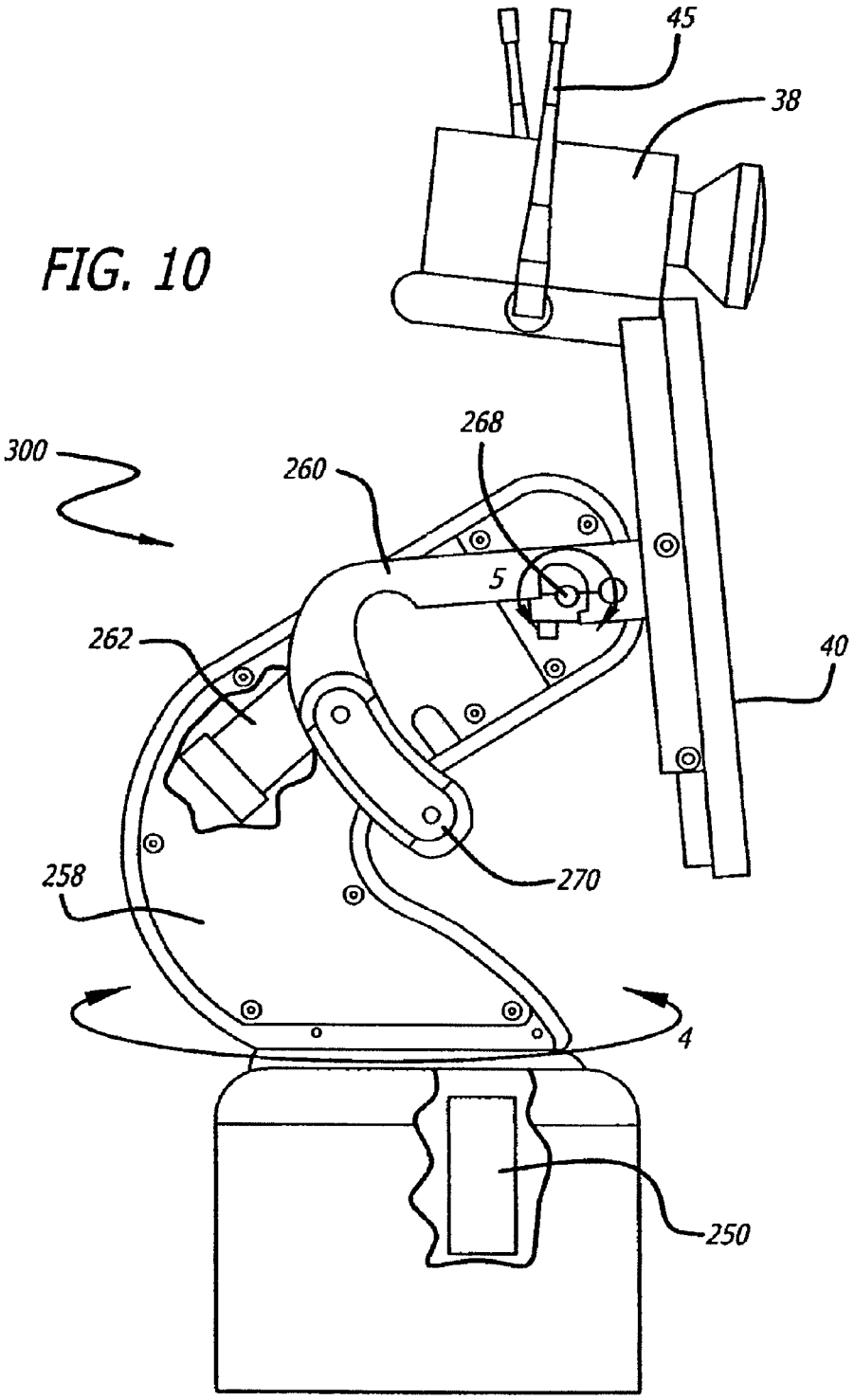
FIG. 10 is a side view of a robot head.

FIG. 10 shows a robot head 300 that can both pivot and spin the camera 38 and the monitor 40. The robot head 300 can be similar to the robot 12 but without the platform 210. The robot head 300 may have the same mechanisms and parts to both pivot the camera 38 and monitor 40 about the pivot axis 4, and spin the camera 38 and monitor 40 about the spin axis 5. The pivot axis may intersect the spin axis. Having a robot head 300 that both pivots and spins provides a wide viewing area. The robot head 300 may be in the system either with or instead of the mobile robot 12. The head 300 may be placed in a patient room to conduct two-way videoconferencing between a patient and a doctor at a remote location. The pivoting and spinning degrees of freedom allow the doctor to move the camera to follow an ambulatory patient.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for [viewing] *enabling at least one of a first remote user and a second remote user to view* a patient *using a robot having a camera and a microphone, the first remote user having an ability to control the robot using a first remote station and the second remote user having an ability to control the robot using a second remote station*, *the method* comprising:

*electing either an exclusive mode of operation or a shared mode of operation, whereby, in the exclusive mode of operation, only of the first remote station and the second remote station has control of the robot and, in the shared mode of operation, both of the first remote station and the second remote station have control of the robot;* generating a first robot movement input command [at a] *using the first* remote station *or the second remote station*;

transmitting the first robot movement input command;

receiving the first robot movement input command at [a] *the* robot that has [a] *the* camera and [a] *the* microphone;

moving the camera to view [a] *the* patient; and, transmitting an image of the patient and a sound of the patient from the robot to the *first* remote station *or the second remote station*.

2. The method of claim 1, further comprising generating a second robot movement command, transmitting the second robot command and moving the robot across a floor of a medical facility.

3. The method of claim 1, wherein the robot movement input command is generated by a doctor.

4. The method of claim 1, further comprising transmitting a video image and a sound of a doctor at the *first* remote station *or the second remote station* to the robot, the video image being displayed by a monitor of the robot, the sound being generated by a speaker of the robot.

5. The method of claim 1, wherein the robot movement input command causes the robot camera to zoom relative to the patient.

6. The method of claim 1, further comprising transmitting a video image of a medical chart from the robot to the *first* remote station *or the second remote station*.

7. The method of claim 1, further comprising generating and transmitting a question from the *first* remote station *or the second remote station* to the robot.

8. The method of claim 7, wherein the question is generated by a speaker of the robot.

9. The method of claim 7, wherein the question is displayed by a monitor of the robot.

10. The method of claim 1, wherein the robot movement input command is transmitted through a broadband network.

*11. The method of claim 1, wherein the robot movement input command is generated by a caregiver.*

*12. The method of claim 1, further comprising detecting when the robot has contacted an object, determining a direction of contact with the object and preventing further movement toward the object.*

*13. The method of claim 1, wherein the robot further comprises a monitor, the monitor and the camera of the robot being mounted to rotate together such that the camera and the monitor cannot be rotated independently of each other, the method further comprising at least one of pivoting and tilting the monitor and the camera together as a single unit.*

*14. The method of claim 4, further comprising compressing, transmitting and receiving the video image and the sound of the first remote user or the second remote user using an MPEG standard.*

*15. The method of claim 1, wherein transmitting the image of the patient and the sound of the patient from the robot to the first remote station or the second remote station comprises transmitting and receiving a video with MPEG compression software.*

*16. The method of claim 1 further comprising*

*displaying the image of the patient on a display connected to the first remote station;*

*transmitting an image of the first user and a sound of the first user from the first remote station to the robot; and*

*displaying the image of the first user on the display connected to the robot.*

*17. The method of claim 16, further comprising accessing information stored in a mass storage device of the robot.*

*18. The method of claim 17, wherein accessing information stored in the mass storage device of the robot comprises accessing medical files associated with the patient.*

*19. The method of claim 17, wherein accessing information stored in the mass storage device of the robot comprises recalling a still picture stored on the robot.*

*20. The method of claim 17, further comprising displaying on the display connected to the first remote station the information stored in the mass storage device of the robot.*

*21. The method of claim 16, further comprising transmitting a command to the robot that causes the robot to move so that the robot is coupled to a battery charger.*

*22. The method of claim 21, wherein the robot couples to the battery charger without human intervention.*

*23. The method of claim 16, further comprising coupling the robot to an electrical wall outlet to recharge the battery.*

*24. The method of claim 16, further comprising moving the robot across a surface through a series of movement input commands that are transmitted from one of the first remote station and the second remote station to the robot.*

*25. The method of claim 24, further comprising creating message packets having multiple data fields, which message packages contain the movement input commands.*

*26. The method of claim 25, further comprising encrypting the message packets that are transmitted to the robot.*

*27. The method of claim 25, wherein one of the multiple data fields is an ID field.*

*28. The method of claim 25, wherein one of the multiple data fields is a forward speed field.*

*29. The method of claim 25, wherein one of the multiple data fields is an angular speed field.*

*30. The method of claim 25, wherein one of the multiple data fields is a stop field.*

*31. The method of claim 25, wherein one of the multiple data fields is a bumper field.*

*32. The method of claim 25, wherein one of the multiple data fields is a sensor range field.*

*33. The method of claim 25, wherein one of the multiple data fields is a configuration field.*

*34. The method of claim 25, wherein one of the multiple data fields is a text field.*

*35. The method of claim 25, wherein one of the multiple data fields is a debug field.*

*36. The method of claim 24, further comprising exclusively controlling the robot from multiple remote stations at different times.*

*37. The method of claim 36, further comprising determining which of the multiple remote stations can have control of the robot.*

*38. The method of claim 16, further comprising moving the display connected to the robot relative to the robot.*

*39. The method of claim 38, wherein moving the display comprises tilting the display connected to the robot.*

*40. The method of claim 38, wherein moving the display comprises rotating the display connected to the robot.*

*41. The method of claim 38, wherein moving the display comprises pivoting the display connected to the robot.*

*42. The method of claim 16, further comprising tilting the camera connected to the robot.*

*43. The method of claim 16, further comprising rotating the camera connected to the robot.*

*44. The method of claim 16, further comprising identifying obstructions to movement using one or more proximity sensors mounted to the robot.*

*45. A method of using a mobile robotic system for facilitating remote monitoring of a plurality of patients in a medical facility having a plurality of patient rooms, including a first patient room and a second patient room, each of the first patient room and the second patient room containing one or more patients, the mobile robotic system comprising a first remote station adapted for use by a first user and a robot configured to be wirelessly linked to the first remote station, the robot comprising a video camera and a microphone, the method comprising:*

*using the first remote station to generate a first set of robot movement input commands that are transmitted to and received by the robot;*

*using the first set of robot movement input commands generated at the first remote station to move the robot to a vicinity of the first patient room;*

*capturing with the video camera of the robot and transmitting to the first remote station patient-related information related to a first patient;*

*after viewing the captured and transmitted patient-related information related to the first patient, using the first*

*remote station to generate a second set of robot input commands that are transmitted to and received by the robot;*

*using the second set of robot input commands generated at the first remote station to move the robot into the first patient room;*

*conducting a two-way videoconference with the first patient in the first patient room using the video camera of the robot, a display of the robot, a video camera of the first remote station and a display of the first remote station, the two-way videoconference including moving the video camera to view the patient, transmitting an image of the patient and a sound of the patient from the robot to the first remote station;*

*using the first remote station to generate a third set of robot input commands that are transmitted to and received by the robot;*

*using the third set of robot input commands generated at the first remote station to move the robot out of the first patient room and into a vicinity of the second patient room;*

*capturing with the video camera of the robot and transmitting to the first remote station patient-related information related to a second patient;*

*after viewing the captured and transmitted patient-related information related to the second patient, using the first remote station to generate a fourth set of robot input commands that are transmitted to and received by the robot;*

*using the fourth set of robot input commands generated at the first remote station to move the robot into the second patient room;*

*conducting a two-way videoconference with the second patient in the second patient room using the video camera of the robot, the display of the robot, the video camera of the first remote station and the display of the first remote station;*

*using the first remote station to generate a fifth set of robot input commands that are transmitted to and received by the robot; and*

*using the fifth set of robot input commands generated at the first remote station to move the robot out of the second patient room.*

*46. The method of claim 45, wherein the patient-related information related to at least one of the first patient and the second patient comprises a patient chart.*

*47. The method of claim 45, wherein using the video camera comprises using a zoom feature to capture the information.*

*48. The method of claim 45, further comprising displaying the first user on the display of the robot during the two-way videoconference.*

*49. The method of claim 45, further comprising using a second station to generate robot input commands.*

*50. The method of claim 49, further comprising selecting only one of the first remote station and the second station to control the robot such that exclusive control of the robot can be provided to one of the first remote station and the second station.*

*51. The method of claim 49, further comprising allowing both the first remote station and the second station to control the robot such that the first remote station and the second station share control of the robot.*

*52. The method of claim 51, further comprising using the first remote station to enable shared control such that both the first remote station and the second station share control of the robot.*

*53. The method of claim 45, further comprising using the first remote station to control a second robot.*

* * * * *